United States Patent
Daniel et al.

(10) Patent No.: US 6,174,307 B1
(45) Date of Patent: Jan. 16, 2001

(54) VIEWING SURGICAL SCOPE FOR MINIMALLY INVASIVE PROCEDURES

(75) Inventors: Steven A. Daniel, Fremont; Stuart D. Harman, San Jose; Timothy C. Reynolds, Mountain View, all of CA (US)

(73) Assignee: Eclipse Surgical Technologies, Inc., Sunnyvale, CA (US)

(*) Notice: Under 35 U.S.C. 154(b), the term of this patent shall be extended for 0 days.

(21) Appl. No.: 09/227,458

(22) Filed: Jan. 8, 1999

Related U.S. Application Data

(60) Division of application No. 09/031,752, filed on Feb. 27, 1998, now abandoned, and a continuation-in-part of application No. 08/794,733, filed on Feb. 3, 1997, now Pat. No. 6,027,497, which is a continuation-in-part of application No. 08/627,704, filed on Mar. 29, 1996, now Pat. No. 5,725,523.

(51) Int. Cl.[7] .................................................. A61B 18/18
(52) U.S. Cl. .................................. 606/15; 606/2; 606/7; 600/103; 600/114; 600/129
(58) Field of Search ................................ 606/2, 7, 13–16, 606/32, 41, 129, 167, 185; 600/114, 103, 127, 125, 121, 129, 153, 160; 604/264, 164, 272, 280

(56) References Cited

U.S. PATENT DOCUMENTS

| | | | |
|---|---|---|---|
| 4,072,147 | 2/1978 | Hett | 128/6 |
| 4,658,817 | 4/1987 | Hardy | 128/303.1 |
| 4,669,467 | 6/1987 | Willett et al. | 128/303.1 |

(List continued on next page.)

FOREIGN PATENT DOCUMENTS

WO 93/20742  10/1993  (WO).

OTHER PUBLICATIONS

Deckelbaum, "Cardiovascular Apps. of Laser Tech.", Lasers in Surgery and Medicine, 15:315–341 (1994).

(List continued on next page.)

*Primary Examiner*—Linda C. M. Dvorak
*Assistant Examiner*—Bryan K. Yarnell
(74) *Attorney, Agent, or Firm*—Ilene Lapidus Janofsky; Ross M. Carothers

(57) ABSTRACT

A viewing and treatment apparatus for performing minimally invasive surgery through an opening in a patient's chest, the apparatus includes a visualization scope with an elongated portion and a distal end, and a working device such as a tissue ablation energy delivery device. The working device is encompassed within a working channel that communicates with the distal end of the scope. In one embodiment, a bronchoscope is used whose catheter shafting includes an introducer sleeve at the distal section of the scope for providing stability during introduction to a patient's chest while stabilizing the treatment and visualization distal ends of the scope at a treatment site. This embodiment can include a needle piercing assembly that cooperatively works with the work device such as for drug delivery. In a second embodiment a rigid endoscope with a viewing channel has an introducer member that is slidably disposed and detachable from the viewing channel and has a transparent convex distal tip which provides non-articulation at the distal end. This introducer member can also be used in conjunction with the first embodiment where the catheter shaft requires non-articulation. Both types of visualization scopes include a working channel in which the working device can translationally egress from the scope's distal end. Additionally, the rigid introducer member can be modified to include a movable transparent rotatable member design for varying the direction which the working devices egresses the apparatus' distal end. The preferred surgical procedure is transmyocardial revascularization and the preferred working device is an optical fiber element that is translatable from the distal end of the apparatus during the procedure. The working device can optionally include a flexible piercing needle with an internal lumen which allows translation of a working device such as an optical fiber or act as a conduit for drug delivery.

77 Claims, 14 Drawing Sheets

U.S. PATENT DOCUMENTS

| | | | |
|---|---|---|---|
| 4,706,656 | 11/1987 | Kuboto | 128/6 |
| 4,718,417 | 1/1988 | Kittrell et al. | 128/303.1 |
| 4,913,142 | 4/1990 | Kittrell et al. | 606/7 |
| 4,967,745 | 11/1990 | Hayes et al. | 128/303.1 |
| 4,976,710 * | 12/1990 | Mackin . | |
| 5,041,108 | 8/1991 | Fox et al. | 606/15 |
| 5,125,926 | 6/1992 | Rudko et al. | 606/19 |
| 5,127,393 * | 7/1992 | McFarlin et al. | 600/114 |
| 5,217,454 | 6/1993 | Khoury | 606/14 |
| 5,249,574 | 10/1993 | Bush et al. . | |
| 5,298,026 | 3/1994 | Chang . | |
| 5,380,316 | 1/1995 | Aita et al. | 606/7 |
| 5,386,817 * | 2/1995 | Jones . | |
| 5,389,096 | 2/1995 | Aita et al. | 606/15 |
| 5,425,355 | 6/1995 | Kulick | 606/14 |
| 5,431,628 | 7/1995 | Millar | 604/100 |
| 5,452,733 | 9/1995 | Steviwan et al. . | |
| 5,470,320 | 11/1995 | Tipfenbiun et al. . | |
| 5,549,601 | 8/1996 | McIntyre et al. | 606/15 |
| 5,562,603 * | 10/1996 | Moll et al. | 600/204 |
| 5,573,531 | 11/1996 | Gregory | 606/14 |
| 5,607,421 | 3/1997 | Jeevluxandeeu et al. . | |
| 5,645,519 * | 7/1997 | Lee et al. | 600/114 |
| 5,713,894 * | 2/1998 | Murphy-Chutorian et al. | 506/7 |
| 5,832,929 * | 11/1998 | Rudko et al. | 606/7 |
| 5,876,329 * | 3/1999 | Harhen . | |
| 6,019,756 * | 2/2000 | Mueller et al. | 606/15 |

OTHER PUBLICATIONS

Frazier et al., "Myocard. Revasc. with Las.", Cullen Cardio. Res. Labs., Tx. Heart Inst., Supp. II C vol. 92, No. 9, II–58–65 (Nov. 1, 1995).

* cited by examiner

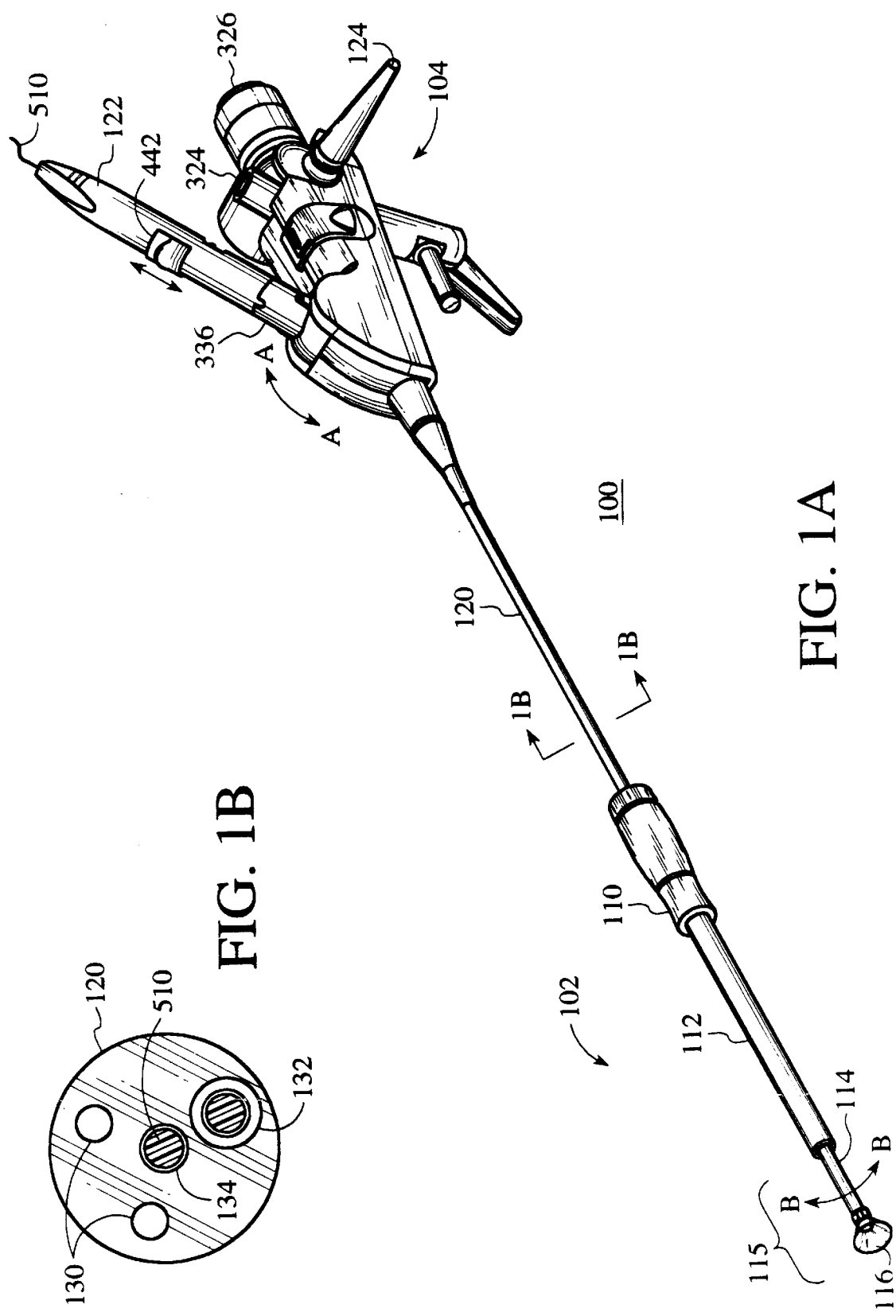

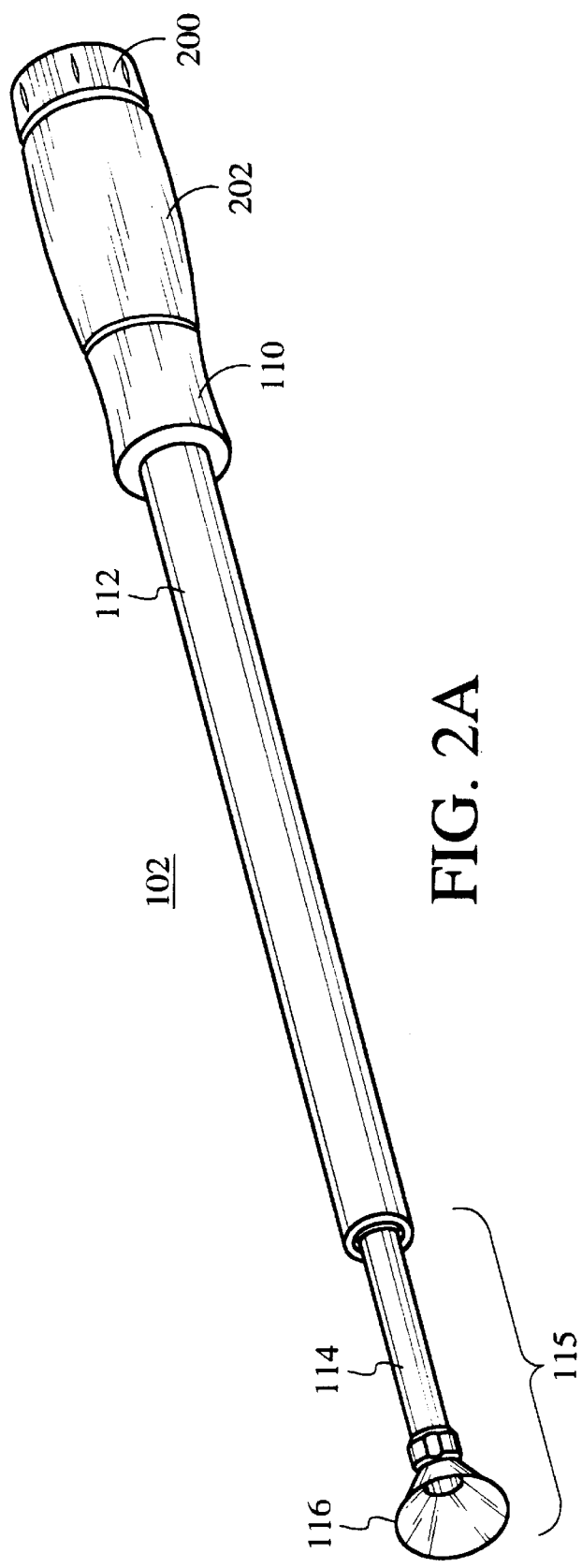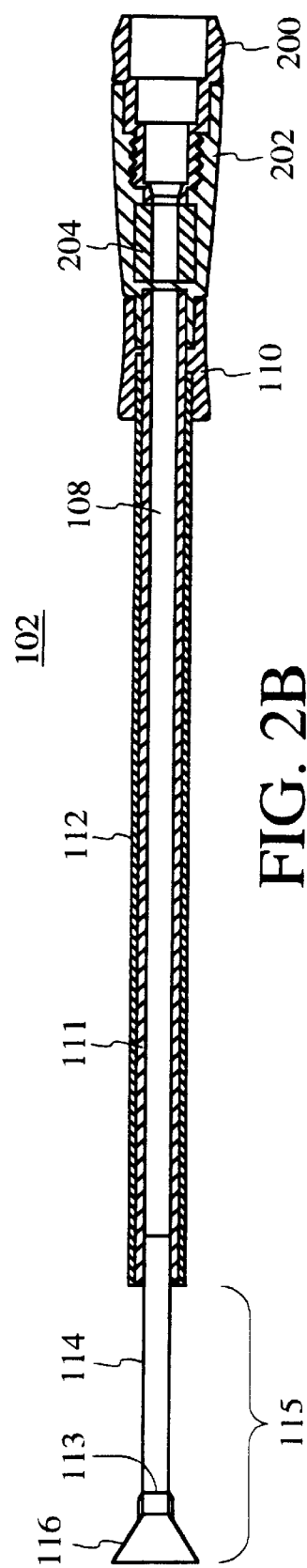
FIG. 2A
FIG. 2B

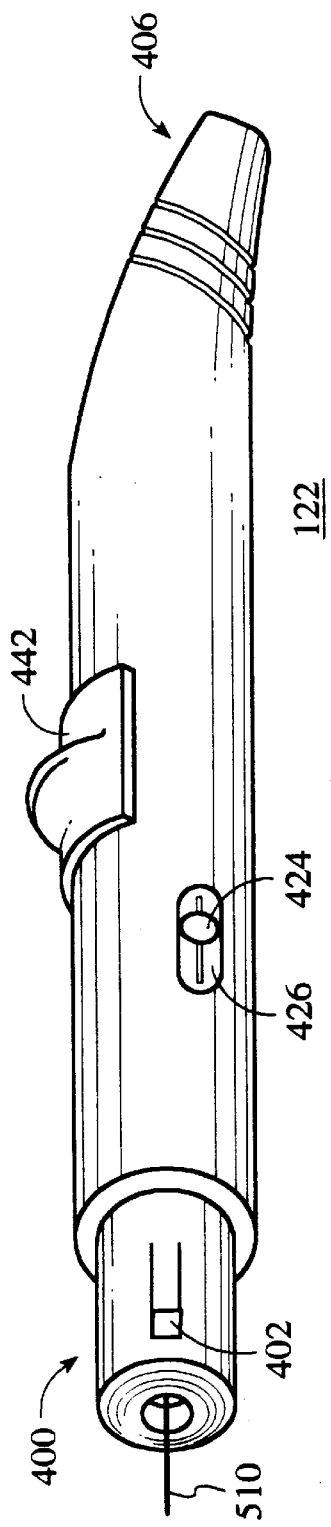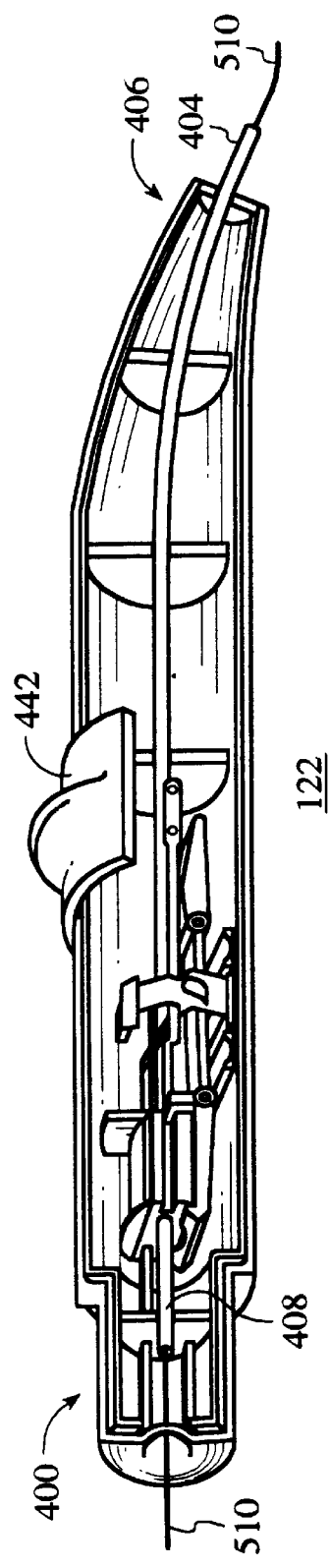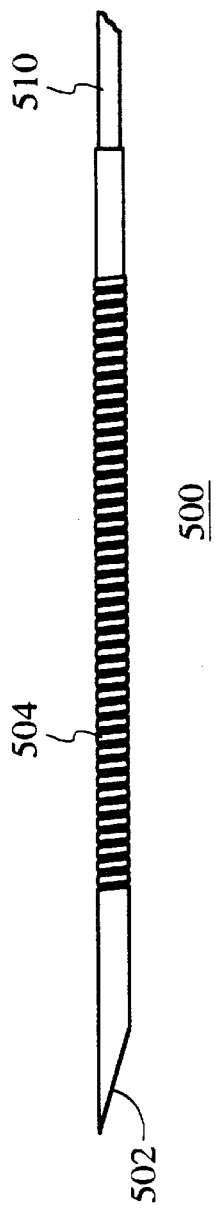
FIG. 4A
FIG. 4B
FIG. 5

VIEWING SURGICAL SCOPE FOR MINIMALLY INVASIVE PROCEDURES

CROSS-REFERENCE TO RELATED APPLICATIONS

This application is divisional of Ser. No. 09/031,752, filed Feb. 27, 1998, now abandoned, and a continuation-in-part (CIP) of Ser. No. 08/794,733 filed Feb. 3, 1997, entitled "MINIMALLY INVASIVE METHOD AND APPARATUS FOR FORMING REVASCULARIZATION CHANNELS", now U.S. Pat. No. 6,027,497, which is a continuation-in-part of Ser. No. 08/627,704 filed on Mar. 29, 1996, entitled "LATERAL-AND POSTERIOR-ASPECT METHOD AND APPARATUS FOR LASER ASSISTED TRANSMYOCARDIAL REVASCULARIZATION AND OTHER SURGICAL APPLICATIONS", U.S. Pat. No. 5,725,523, which are all incorporated by reference herein.

BACKGROUND OF THE INVENTION

1. Field of the Invention

This invention relates to a viewing surgical scope apparatus capable of introducing a visualization scope and a working device such as an energy delivery device in minimally invasive surgical procedures. In particular, the preferred procedure is transmyocardial revascularization "TMR" wherein the energy delivery device is an optical fiber element.

2. Discussion of Related Art

The human heart is a muscular dual pump that beats continuously throughout life sending blood to the lungs and the rest of the body. The interior of the heart consists of four distinct chambers. The septum, a thick central muscular wall, divides the cavity into right and left halves. On the right side, the upper half is known as the right atrium. Deoxygenated blood from the rest of the body arrives in the right atrium via the vena cava, the blood is pumped across a one-way valve known as the tricuspid valve into the lower portion known as the right ventricle. From there the blood circulates to the lungs through the pulmonary valve via the pulmonary artery where it is oxygenated by circulation through the alveoli of the lungs (not shown). The blood returns via the pulmonary veins to the left atrium and flows through a second valve, the mitral valve into the left ventricle where it is pumped via the aorta to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium, oxygenated blood is returned from the lungs to the left atrium. During atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's autonomic nervous system.

Though the heart supplies blood to all other parts of the body, the heart itself has relatively little communication with the oxygenated blood supply. Thus, the two coronary arteries, the left coronary artery and the right coronary artery, arise from the aorta and encircle the heart muscle on either side "like a crown" to supply the heart itself with blood.

Heart disorders are a common cause of death in developed countries. They also impair the quality of life of millions of people and restrict activity by causing pain, breathlessness, fatigue, fainting spells and anxiety. The major cause of heart disease in developed countries is impaired blood supply. The coronary arteries become narrowed due to atherosclerosis and part of the heart muscle is deprive of oxygen and other nutrients. The resulting ischemia or blockage can lead to angina pectoris; a pain in the chest, arms or jaw due to lack of oxygen to the heart's myocardium, or infarction; or tissue necrosis in myocardial tissue.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve clots) can be very effective. If drug treatment fails transluminal angioplasty is often indicated—the narrowed part of the artery, clogged with atherosclerotic plaque or other deposits, can be stretched apart by passing a balloon to the site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion, thereby requiring emergency procedures, the procedure known as coronary artery bypass grafting (CABG) is the most common and successful major heart operation performed, with over 500,000 procedures done annually in America alone. The procedure takes at least two surgeons and can last up to five hours. First, the surgeon makes an incision down the center of the patient's chest and the heart is exposed by opening the pericardium. A length of vein is removed from another part of the body. The patient is subjected to cardiopulmonary bypass during the operation. The section of vein is first sewn to the aorta and then sewn onto a coronary artery at a place such that oxygenated blood can flow directly into the heart. The patient is then closed. Not only does the procedure require the installation of the heart-lung machine, a very risky procedure, but the sternum must be sawed through and the risk of infection is enhanced during the time the chest cavity is spread open.

Another method of improving myocardial blood supply is called transmyocardial revascularization (TMR), the creation of channels from the epicardial to the endocardial portions of the heart. The procedure uses needles to perform "myocardial acupuncture," that has been experimented with at least as early as the 1930s and used clinically since the 1960s, see Deckelbaum. L. I., Cardiovascular Applications of Laser Technology, *Lasers in Surgery and Medicine* 15:315–341 (1994). This technique has relieved ischemia by allowing blood to pass from the ventricle through the channels either directly into other vessels perforated by the channels or into myocardial sinusoids which connect to the myocardial microcirculation. This procedure has been likened to transforming the human heart into one resembling that of a reptile. In the reptile heart, perfusion occurs via communicating channels between the left ventricle and the coronary arteries. Frazier, O. H., Myocardial Revascularization with Laser—Preliminary Findings, *Circulation,* 1995; 92 [suppl II:II-58-II-65]. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is not well understood.

Numerous TMR studies have been performed using lasers where channels are formed in the myocardium. In one study, 20–30 channels per square centimeter were formed into the left ventricular myocardium of dogs prior to occlusion of the arteries. LAD ligation was conducted on both the revascularized animals as well as a set of control animals. Results showed that animals having undergone TMR prior to LAD ligation acutely showed no evidence of ischemia or infarction in contrast to the control animals. After sacrifice of the animals post operatively between 4 weeks and 5 months, the laser-created channels could be demonstrated grossly and microscopically to be open and free of debris and scarring.

It is possible that the creation of laser channels in the myocardium may promote long-term changes that could augment myocardial blood flow such as by inducing angiogenesis in the region of the lazed (and thus damaged) myocardium. Support for this possibility is reported in histological evidence of probable new vessel formation adjacent to collagen occluded transmyocardial channels. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the inside of the laser channels is or can become hemocompatible and that it resists occlusion caused by thrombo-activation and/or fibrosis.

U.S. patents that deal with TMR and myocardial revascularization include U.S. Pat. No. 4,658,817 which teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforated a portion of tissue to provide the laser beam direct access to distal tissue. U.S. Pat. No. 5,125,926 teaches a heart-synchronized pulsed laser system for surgical TMR. This patent's system and method include a sensing device for synchronized firing of a laser during the contraction and expansion of a beating heart during a predetermined portion of the heartbeat cycle. This heart-synchronized pulsed laser system is important where the type of laser, the energy and pulse rate are potentially damaging to the beating heart or its action. Additionally, as the heart beats, the spatial relationship between the heart and the tip of the laser delivery probe may change so that the necessary power of the beam and the required position of the handpiece may be unpredictable. U.S. Pat. No. 5,380,316 teaches of TMR performed by inserting a portion of an elongated flexible lasing apparatus into the chest cavity of a patient and lasing channels directly through the outer surface of the epicardium into the myocardium tissue. U.S. Pat. Nos. 5,389,096 and 5,607,421 teach of myocardial revascularization that is performed by guiding an elongated flexible lasing apparatus into a patient's vasculature percutaneously such that the firing end of their respective lasing apparatus are adjacent the endocardium for lasing channels directly through the endocardium into myocardium tissue without perforating the heart's pericardium layer. None of the above listed patents teach methods for performing myocardial revascularization using minimally invasive surgical techniques, nor do their respective system's include a device for visualizing areas of the heart during such a procedure.

Patent literature that deals with minimally invasive surgical procedures for myocardial revascularization includes PCT application WO 97/13468 and U.S. Pat. No. 5,700,259 which teach of thoracoscopic myocardial revascularization devices using a $CO_2$ type laser based handpiece. U.S. Pat. No. 5,685,857 teaches of a thoracoscopic cannula device. PCT application WO 97/34540 teaches of video assisted thoracoscopic $CO_2$ type laser TMR surgical method for a thoracoscopic myocardial revascularization procedure.

Finally, viewing devices used in cardiac interventional procedures include U.S. Pat. Nos. 4,784,133 and 4,976,710 which both teach of an angioscope/bronchoscope device that includes a flexible distal end with an inflatable balloon structure for viewing intravasculature structures. This device's flexible catheter includes a working channel for introducing a procedural device at the viewing/treatment distal end.

There is a need for an apparatus and method for performing myocardial revascularization from one or more minimally invasively formed penetrations and eliminating the need for open chest surgery by providing a viewing surgical scope allowing for single handed use during such a procedure.

SUMMARY OF THE INVENTION

The present invention provides a method and apparatus for performing a minimally invasive surgical (MIS) procedure and in particular for the creation of a TMR channels in a heart wall. The surgical viewing scope apparatus comprises a visualization device such as a bronchoscope or endoscope in combination with a working device such as an optical fiber element or other energy delivery device which is introduced through a minimally invasive formed penetration of a patient's chest. The preferred use of the apparatus is to deliver sufficient energy to the heart wall to form a channel through at least a portion of the heart wall wherein the energy delivery device is introduced through a minimally invasive formed penetration in the patient's chest.

The first viewing surgical scope embodiment is an articulating bronchoscope with a mid-section introducer sleeve assembly for placement of the distal end of the viewing surgical scope through a patient's chest penetration. This embodiment of the viewing surgical scope has an integrated working channel and an integrated handle member for providing both advancement of the working device and articulation of the distal end of the viewing surgical scope from which a working device can egress.

The second viewing surgical scope embodiment is a rigid endoscope with various designs of the working channel from which the working device can egress from the viewing surgical scope. This second embodiment includes a closed ended introducer sleeve member with a preferred convex viewing tip that can be pushed against the heart and allows viewing of a beating heart while performing the operation. This sleeve member acts as an introducer tubular member that also stops bleeding by applied pressure and can perform multiple operative procedures from the same chest wall penetration. This second embodiment can also include a pistol grip hand-piece with members for advancement and actuation of the working device. The introducer tubular member allows for quick disconnect and interchangeability for operating on both lateral, anterior and posterior sides of the heart from a single penetration in a patient's chest. The introducer tubular member is either a disposable or reusable member.

The method of the invention includes introducing a first viewing surgical device through a first minimally invasive penetration of a patient's chest. The first viewing surgical device includes a working channel. An energy delivery device is introduced through the working channel of the first viewing surgical device. Sufficient energy is delivered from the energy delivery device to the wall of the heart to form a channel through at least a portion of the wall. Another embodiment of the method includes forming first, second and third minimally invasive penetrations in a patient's chest. A first viewing scope device is introduced through the first minimally invasive penetration. The heart is prepared for channel formation by using tools introduced through the second and third minimally invasive penetrations. A second visualization device includes a working channel and is introduced through the third minimally invasive penetration. An energy delivery device is introduced through either the second minimally invasive penetration or the working channel of the second viewing surgical scope device. Sufficient energy from the energy delivery device is delivered to the heart wall and create a channel through at least a portion of the wall. The positioning of the visualization devices and the working tools can be interchanged between the first, second and third minimally invasively formed penetrations.

An object of the invention is to provide an apparatus and method using a minimally invasive surgical technique for TMR.

Another object of the invention is to provide a method and apparatus for performing TMR through at least one minimally invasively formed penetration of a patient's chest.

Another object of the present invention is to provide a method and apparatus for TMR through two or more minimally invasively formed penetrations of a patient's chest.

Another object of the present invention is to provide a method and apparatus for TMR through a minimally invasively formed penetration in a patient's chest with an articulating viewing bronchoscope that includes at least one working channel, wherein multiple working channels could be incorporated for other procedural devices, such as a piercing needle for drug delivery at treatment sites.

Another object of the present invention is to provide a method and apparatus for TMR through first and second minimally invasively formed penetrations in a patient's chest with a viewing surgical scope in the first penetration and a trocar configured to introduce working tools through the second penetration.

Another object of the invention is provide a method and apparatus for TMR by forming one or more minimally invasively formed penetrations and providing access to more than one region of the heart.

Another object of the present invention is to provide an apparatus for minimally invasive surgery (MIS) which is sufficiently rigid to support surrounding tissue, which allows channels to be created at angles to the apparatus' axis, e.g. normal to target tissue, or at an oblique angle to the target tissue site.

Yet another object of the present invention is to provide an apparatus for TMR which is atraumatic to surrounding tissue, minimizes bleeding, and reduces tissue movement at a target tissue site.

Another object of the present invention is to provide an apparatus having enhanced use and functional capabilities, such as a tissue piercing capability for added stability during the TMR procedure or drug delivery use.

These and other objects of the invention are achieved in a method for a closed-chest formation of a channel in a wall of a heart. An energy delivery device is introduced through a first minimally invasive penetration of a patient's chest. Sufficient energy is delivered from the energy delivery device to the wall of the heart to form a channel through at least a portion of the wall. In its simplest embodiment, a conventional pneumo-needle may be inserted through the chest wall and a laser waveguide inserted therethrough to form a channel, preferably using a viewing device to show the position of the advancing waveguide and the heart wall.

Numerous other advantages and features of the present invention will become readily apparent from the following detailed description of the invention and the embodiments thereof, from the claims and from the accompanying drawings.

BRIEF DESCRIPTION OF THE FIGURES

FIG. 1A is a representative isometric view of a first embodiment of the viewing surgical scope apparatus of the present invention using articulated distal section members.

FIG. 1B is a section view of viewing surgical scope apparatus shown in FIG. 1A.

FIG. 2A is an isometric view of the distal end of the viewing surgical scope's introducer assembly shown in FIG. 1A.

FIG. 2B is a section view of FIG. 2A.

FIG. 4A is an isometric view of the optical fiber advancement and control handle assembly of the viewing surgical scope apparatus shown in FIG. 1A.

FIG. 4B is a section view of FIG. 4A.

FIG. 5 is a representative side view of a piercing needle assembly used with the embodiments of the invention's viewing surgical scope apparatus.

Figure 2C:
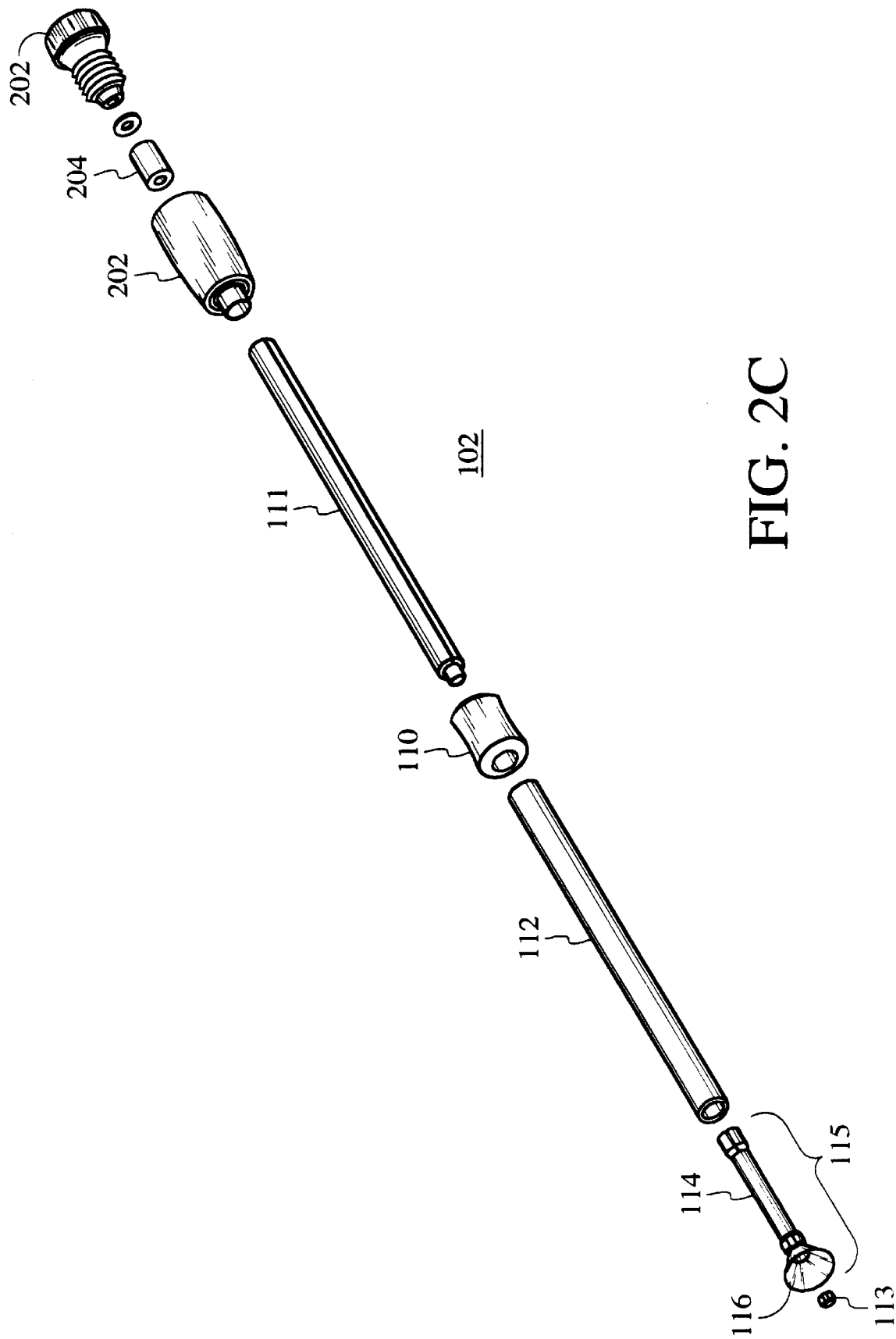
FIG. 2C is an exploded view of the distal end of the viewing surgical scope shown in FIG. 2A.

It will be understood that the invention's preferred embodiments have many of the individual elements whose functional aspects are similar. Thus, it will be understood that structural elements having similar or identical functions may have like reference numerals associated therewith. The appended drawings illustrate only typical embodiments of this invention and are therefor not to be limiting of its scope, for the invention may admit to other equally effective embodiments.

DETAILED DESCRIPTION

A minimally invasively formed penetration is a chest penetration that does not entail "open chest" surgery by gross spreading of the ribs or cutting through excessive ribs and/or the sternum. Minimally invasive surgery also involves formation of penetrations that may be performed intercostally or non-intercostally to access tissues and organs without large incision openings in a patient. Once devices have been introduced in this manner, treatments may be affected from within an organ outwards, i.e. "inside-out," or in an "outside-in" manner. "Channels" refer to revascularization entries through the epicardium or myocardium and further includes entries that extend (i) through the endocardium from the epicardium; (ii) partially or fully through the myocardium; (iii) to form stimulation zones; or (iv) to form drug pockets. "Working devices" for attached either permanently to or slidably disposed within the tube 112. Flexible tubular member 114 in turn is attached to the cup member 116. The optional inner tube 111 is attached to the flexible tubular member 114 and the inner tube 111 is slidably disposed within the tube 112. The inner tube 111 is made integral with the tube 112 when the tubular member 114 is permanenetly attached to tube 112. Tube 111 when used attaches to the collet housing 202, otherwise the tube 112 is attached thereto. The distal end of the catheter 120, not shown in FIGS. 2A–2C, is disposed inside inner tube 111 and flexible tube 114 in the bore 108. The catheter 120 is secured to the introducer tubular assembly 102 at a fixed location by manually tightening collet thumbscrew 200 into collet housing 202, which compresses gripper 204. A distal end lock ring 113 attaches the distal end of the catheter 120 to the cup member 116 as shown in FIG. 2C. The flexible tubular member 114 can be drawn into the tube 112 by making the cup member 116 smaller then shown such that when handle 110 can be decoupled from the collet housing 202 by twisting the handle 110 and then pushing handle member 110 with tube 112 towards the distal end of the scope 100, the cup member 116 collapses and resides within the tube 112 thereby providing ease of scope 100 positioning through a minimally invasively formed penetration in a patient's chest so that entanglement with other instruments or internal body parts is minimized.

The flexible tubular member 114 and the suction cup member 116 form distal end assembly 115. This articulating distal end assembly 115 is disconnectable and interchangeable with a essentially rigid non-articulating viewing tubular assembly 600 discussed below and shown in FIGS. 6A–6D for a viewing surgical scope apparatus. The introducer tubular assembly 102 with catheter 120 is for insertion into a patient's chest through a minimally invasive penetration using the handle 110 for emplacement, see U.S. Pat. No. 6,027,497, which teaches of a trocar used for initially providing a chest wall penetration for introducing instruments into a chest cavity.

Catheter 120 comprises the elongated shafting of a bronchoscope or flexible endoscope tubing. The introducer tubular assembly 102 provides: a) stable support for emplacement within a patient's chest cavity and b) prevents unintended rotation and axial movement of the distal end of a working device such as the laser energy delivery optical fiber element 510. The flexible tubular member 114 allows deflection at the distal end of the scope 100 by pivotal motions of the handle 122 which in turn causes a pivotal joint indicated by double arrow A—A in FIG. 1A to push or pull a control wire (not shown) or an equivalent translational member communicating between the bronchoscope's proximal body assembly 104 and the distal end of the catheter 120. Tip deflection mechanisms in bronchoscopes are well known in the art. The flexible tubular member 114 can be made of flexible silicon rubber or other elastic material with flexural characteristics for providing the necessary stability on a beating heart. Cup member 116 can optionally communicate with a vacuum treatment and diagnosis of affected coronary/vasculature tissue include devices configurable and extendable through a lumen within the viewing surgical scope's distal end such as: optical fiber elements capable of delivering laser energy with or without a piercing needle assembly at the distal end of the viewing surgical scope, drug delivery using a piercing needle assembly, RF tissue ablation devices, ultrasound devices, or mechanical coring devices.

FIG. 1A is a representative isometric view of the first embodiment of the invention's viewing surgical scope 100. The viewing surgical scope 100 is an articulating bronchoscope with a distal end introducer assembly 102 and a main body assembly 104. The introducer assembly 102 includes a handle portion 110 coupled to an essentially rigid tube 112. Tube 112 surrounds a flexible member 114 with an attached suction cup 116 member. Catheter 120 couples to the main body assembly 104 and is either rigid, semi-rigid or flexible. A control handle 122 provides control of an optical fiber advancement member 442 of an optical fiber element 510 which transmits laser energy from a remote laser energy source. The bronchoscope's catheter 120 has multiple conduits which are accessed through the main body assembly 104 via multiple portal openings such as a fiber optic waveguide portal opening 124. These conduits accomplish functions such as illumination, aspiration or irrigation of target tissue at the scope's distal end at suction cup member 116. A hollow working channel is included within the catheter 120 for introducing implements such as a laser energy delivery optical fiber. The visualization scope shown can be a standard articulating bronchoscope or custom designed flexible endoscope made by Storz, Olympus or Pentax. The visualization scope's catheter 120 is within the bore 108 of the introducer assembly 102 shown in FIG. 2B.

FIG. 1B is a section view at sectional line 1B—1B of the viewing surgical scope 100 shown in FIG. 1A. The catheter 120 is a shaft of a bronchoscope with conduits 130 and visualization lumen with internal fiber 132 & working channel 134 with internal laser energy optical fiber element 510 extending the length of catheter 120 that communicates between the main body assembly 104 and the end at cup member 116. In a typical configuration, one or more conduits 130 can be included within the catheter 120. An eyepiece 326 shown in FIG. 1A observes target tissue at the distal end of the viewing surgical scope 100 via the visualization lumen with internal imaging fiber 132. Various types of ancillary viewing capabilities such as CCD monitoring can be attached at the eyepiece 326. A translatable laser energy optical fiber element 510 is translatable and is disposed within the working channel 134 to deliver laser energy at the distal cup member 116 to form TMR channels in the heart.

FIGS. 2A, 2B & 2C show the introducer tubular assembly 102 of the viewing surgical scope 100 shown in FIG. 1A. Handle member 110 couples, either by threaded member for quick uncoupling or permanently coupled thereto, to an essentially rigid tube 112. A flexible tubular member 114 is source attached to the proximal body assembly 104 through port 324 via one of the internal conduits 130 to assist in heart wall attachment. Cup member 116 provides a broad surface which locks on the heart when evacuated for stability during the procedure. Cup member 116 keeps the optics clean and provides a protective shield for sharp tools which can scratch adjacent heart tissue. The cup member 116 can equivalently be a flange member with a flexible grooved annular surface for locking onto a heart surface with or without vacuum assist or be a flange member with a gripping textured surface that attaches to tissue during the procedure.

Figure 3A:
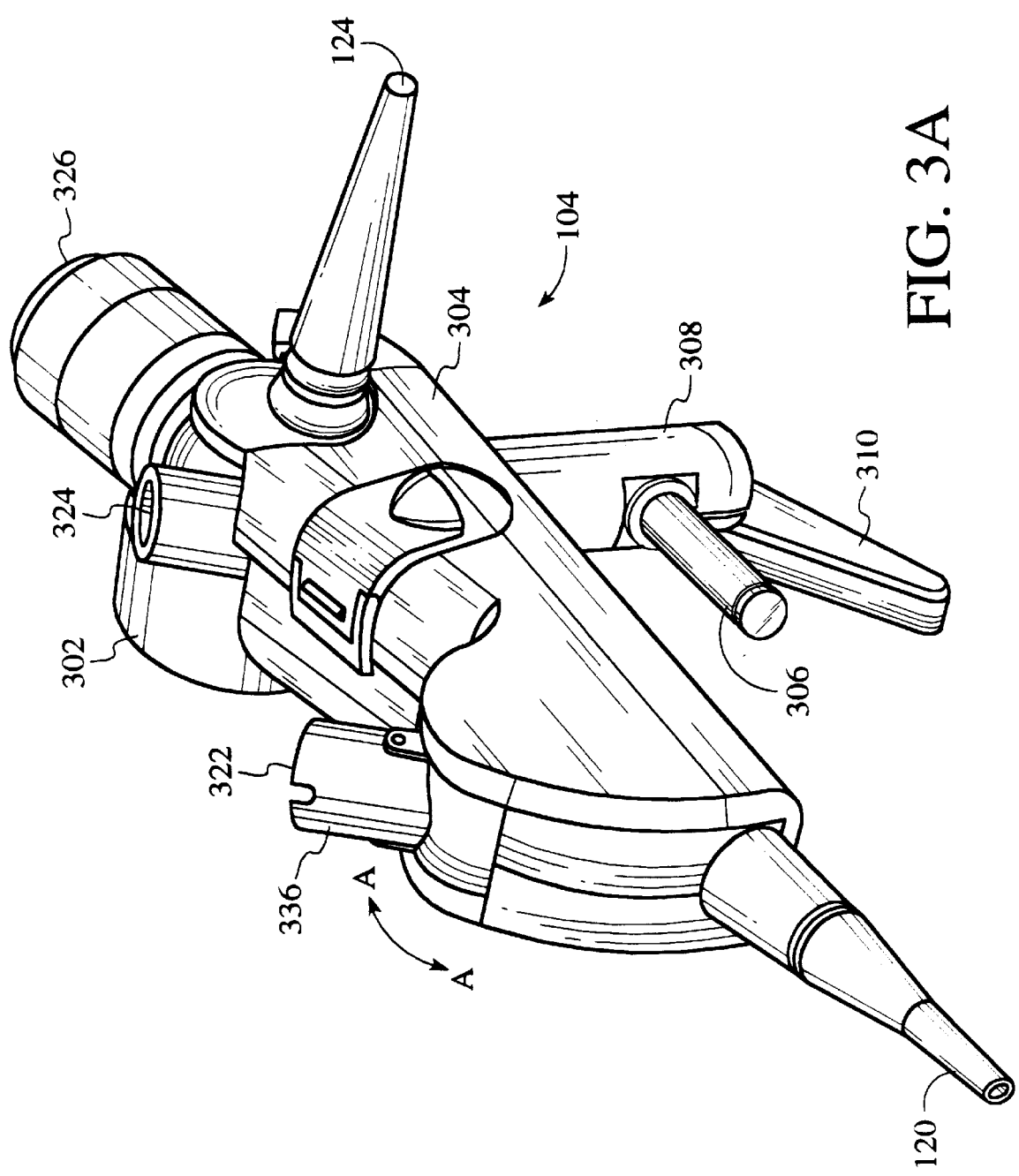
FIG. 3A is an isometric view of the proximal end of the viewing surgical scope apparatus shown in FIG. 1A.
Figure 3B:
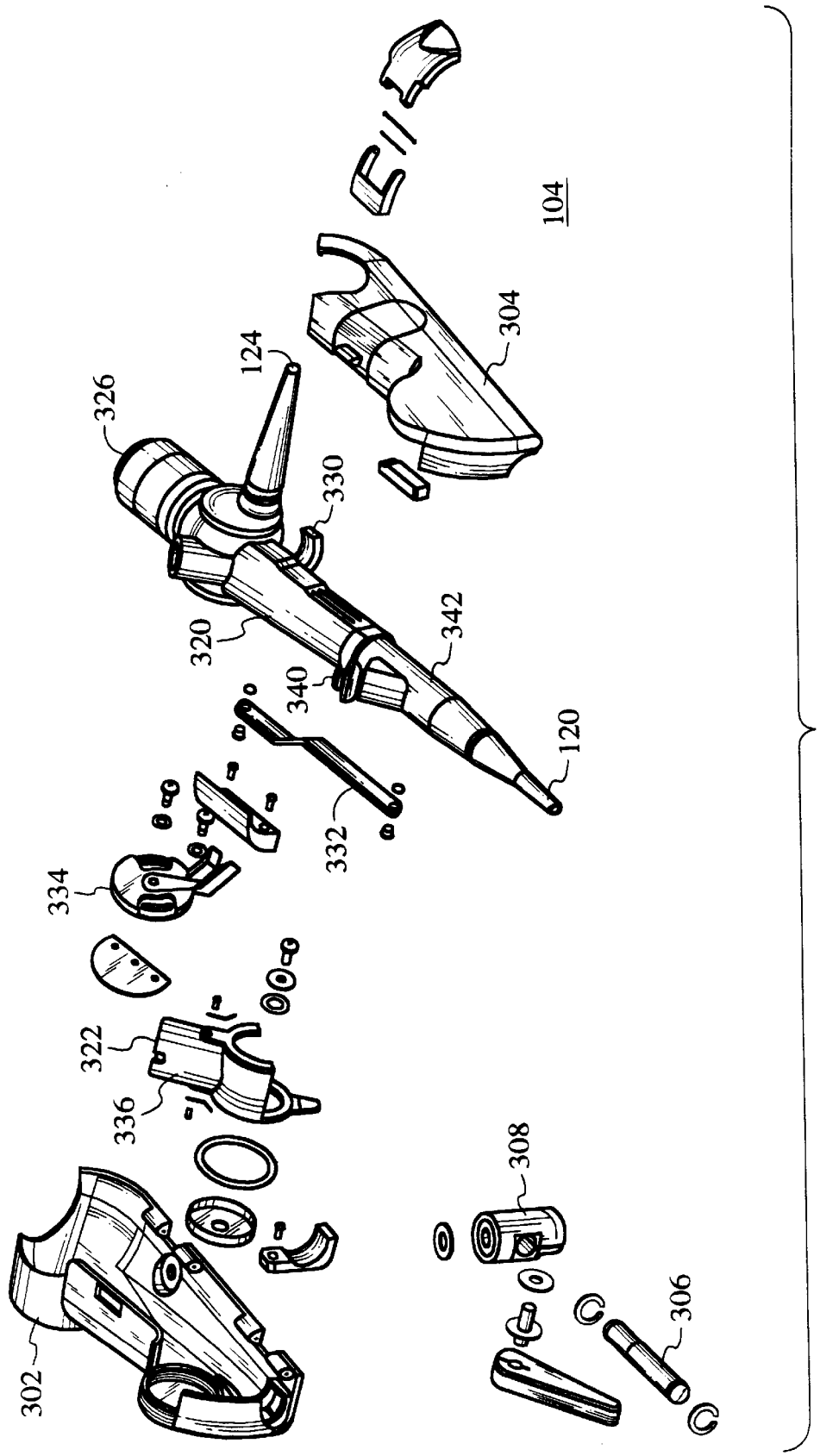
FIG. 3B is an exploded view of FIG. 3A.

FIGS. 3A & 3B are views of the main body assembly 104 as shown in FIG. 1A that can be mounted to the operating table or other structure using mounting shaft 306 that is attached to the body mount 308. The body mount handle 310 allows manipulation of the main body assembly 104 when mounted to a fixture where the practitioner uses one hand to hold the introducer tube 112 at handle 110 and the other hand controls the handle 122 for optical fiber 510 translations and/or deflections of the distal end's cup member 116. Main body assembly 104 in exploded view shown in FIG. 3B has a right body housing 302 and a left housing body 304. The right and left body housings 302 and 304 are configured as mating halves of an outer housing that encompass the proximal end of the visualization scope 342, which is an articulating-type bronchoscope in this embodiment of the invention. The visualization scope 342 has at least two channels wherein a first working channel portal 322 communicates with the working channel 134 and the visualization portal through eyepiece 326. A CCD-camera can optionally be used via the eyepiece 326. Portal opening 124 typically provides illumination at target tissue sites at the distal end cup member 116. Linkage 332 couples lever 330 via wheel linkage 334 to handle pivot member 336. Pivoting of handle 122 shown by double headed arrow A—A in FIG. 1A results in articulation of the flexible member section 114 via control lever 330 action. The working channel port 322 optionally allows introducing procedural tools and instruments including but not limited to scissors, graspers, fiber optic tools, suture mechanisms without the pivot arm assembly as shown. Working channel port 322 with the handle 122 feature as discussed above substantially aligns with and allows free movement of the handle pivot member 336 through a ball joint socket design that couples to the port 340 on visualization scope 342. Handle pivot member 336 allows translatation of the working device such as an optical fiber element 510 therethrough.

Figure 4C:
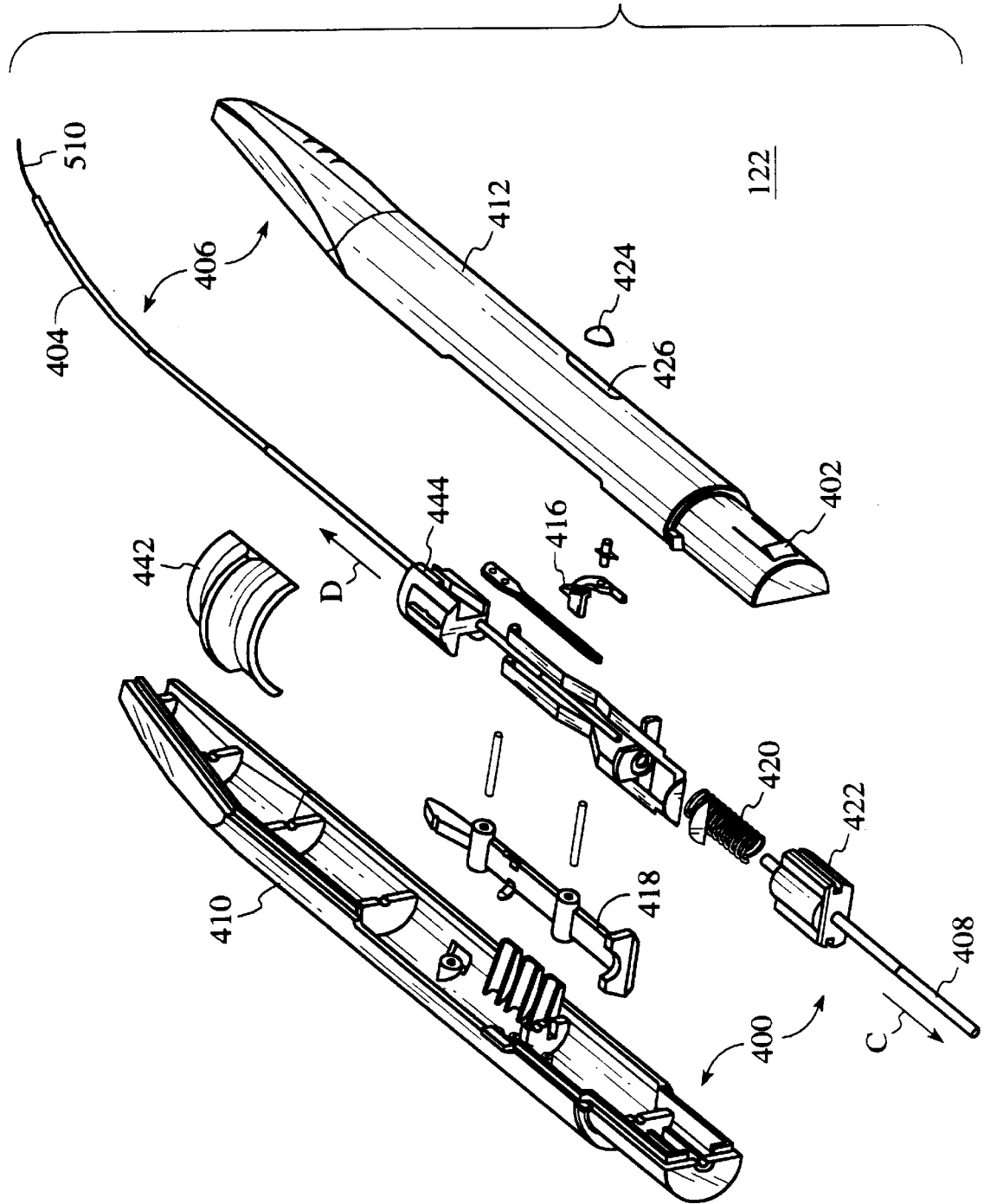
FIG. 4C is an exploded view of FIG. 4A.

FIGS. 4A & 4B are partial component views of the handle 122 with the optical fiber element thumb slider 442 shown in FIG. 1A. FIG. 4B shows the handle 122 without the spring biasing element 420 and an interposed triggering/retraction leaf spring member and an internal slider 444 for clarity. FIG. 4C is an exploded view showing the internal components of the handle 122. The thumb slider 442 advances and retracts the energy delivery device such as the optical fiber 510 independent of the triggered piercing needle member assembly as shown in FIG. 5. The handle 122 as discussed above moves in unison with handle pivot 336 shown in FIG. 1A thereby providing articulation of distal tip cup 116. The practitioner's hand can control both the advancement of the optical fiber 510 and articulation of the distal tip cup member 116. The distal end 400 of handle 122 is inserted into pivot handle member 336 and retained in place by locking member 402. An end tube 404 sleeve enters the handle 122 at its proximal end 406 and another similar distal end tube 408 sleeve is disposed at the distal end 400 and extends to the distal end of the scope 100. A mating right handle portion 410 and a left handle portion 412 are coupled together and enclose a needle piercing spring loaded drive assembly and energy delivery device advancement and control components. The optical fiber element 510 passes through the proximal and distal ends through tube 404 and a needle advance tube 408 which telescope with each other, the tube 404 is smaller than the tube 408 and the tube 404 attaches to the optical fiber element 510, the tube 404 attaches internally to the internal slider 444 and the tube 404 slides within the tube 408, thus allowing translation of the optical fiber 510 independent of the tube 408 movement. Movement of thumb slider 442 in direction C disengages a ratchet 416 in mechanical cooperation with a flexible latch 418 distal end locking member that disengages a piercing needle slider 422 resulting in needle advance spring 420 to push the needle slider 422 forward causing the needle advance tube 408 to move in direction C as well to advance the piercing needle distal end assembly 500 as shown in FIG. 5. Continued forward movement of thumb slider 442 advances the fiber optic element 510 through the needle advance end tube 408 which remains stationary. Movement of the thumb slide 442 is limited by fiber advance and depth stop button 424 slidably disposed within slot 426 by either a threaded compression or a biased detent member that cooperatively engages the slot 426 at predetermined positions. Finally, retraction of advance thumb slider 442 in the direction of arrow D causes the internal slider 444 to move rearwardly and causes the distal end of the triggering/retraction leaf spring member, which cooperatively slides within and engage internal slots in the slider 444, to engage the distal end face of the slider 444 and pull the piercing slider 422 rearwardly as well, thus resetting and latching the needle slider 422 with spring 420 in relation to the latch 418 distal end face. The tube 408 is inserted into the working channel of the inventions viewing surgical scope apparatus.

FIG. 5 is a representative side view of the piercing needle assembly's distal end 500. Piercing needle end portion 502 has a bevel cut end for piercing tissue and is coupled to a flexible section 504 which allows passage of the piercing needle distal end assembly 500 through a working channel with bending such as a flexible catheter or pre-shaped tubing. A fiber optic element 510 or other energy delivery device 510 passes through a lumen within piercing needle assembly 500 as shown in FIGS. 4A, 4B and 5. Moreover, the distal end needle assembly 500 can be a flexible drug delivery conduit and be a working device for the invention's viewing surgical scopes. Similarly, the distal end piercing needle assembly 500 can be replaced with a piercing optical fiber element as taught in U.S. Pat. No. 5,703,985 entitled "Optical Fiber Device and Method for Laser Surgery Procedures," which is hereby incorporated by reference.

Figure 6A:
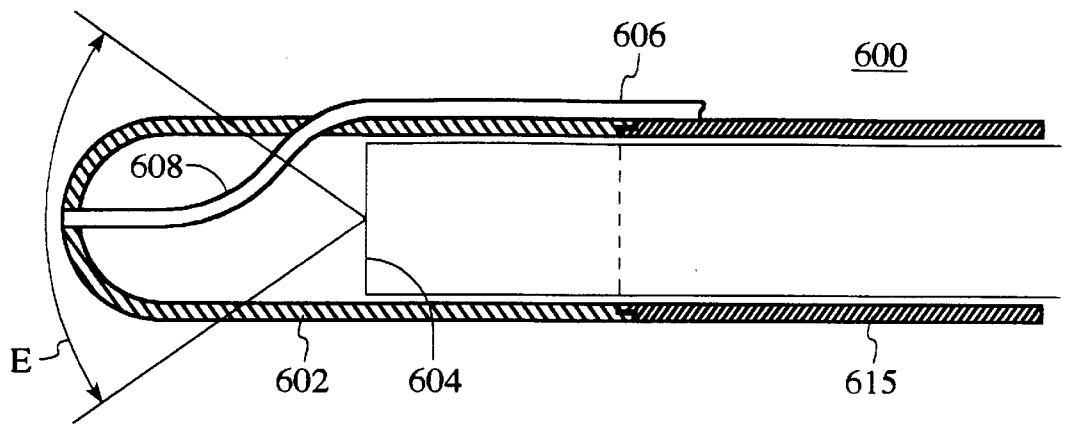
FIGS. 6A, 6B, 6C & 6D are representative section views of viewing tubular assemblies that each have a clear distal tipped section with a working channel having various orientations at the clear distal tip.
Figure 6B:
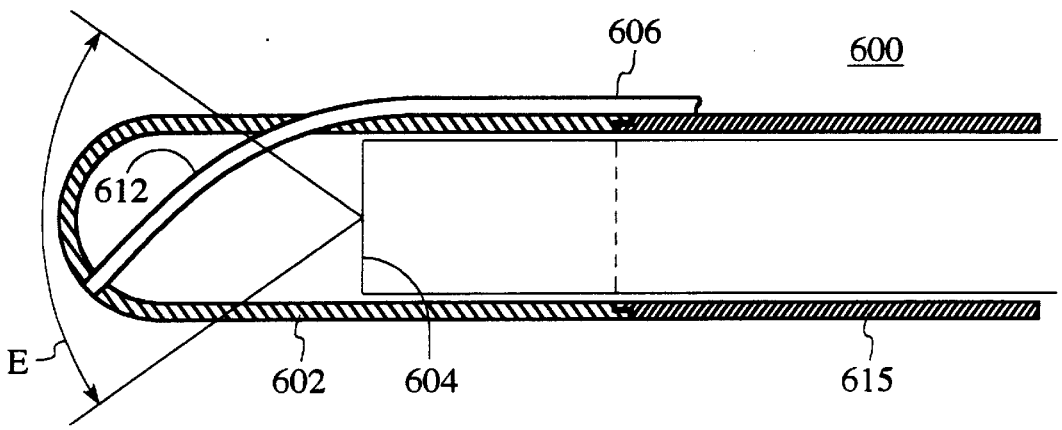
Figure 6C:
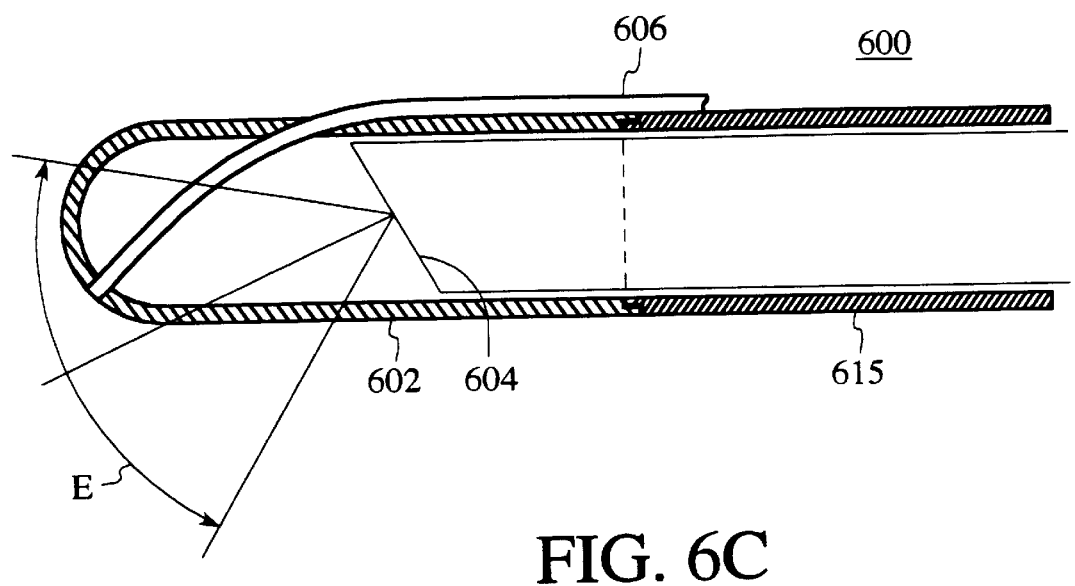
Figure 6D:
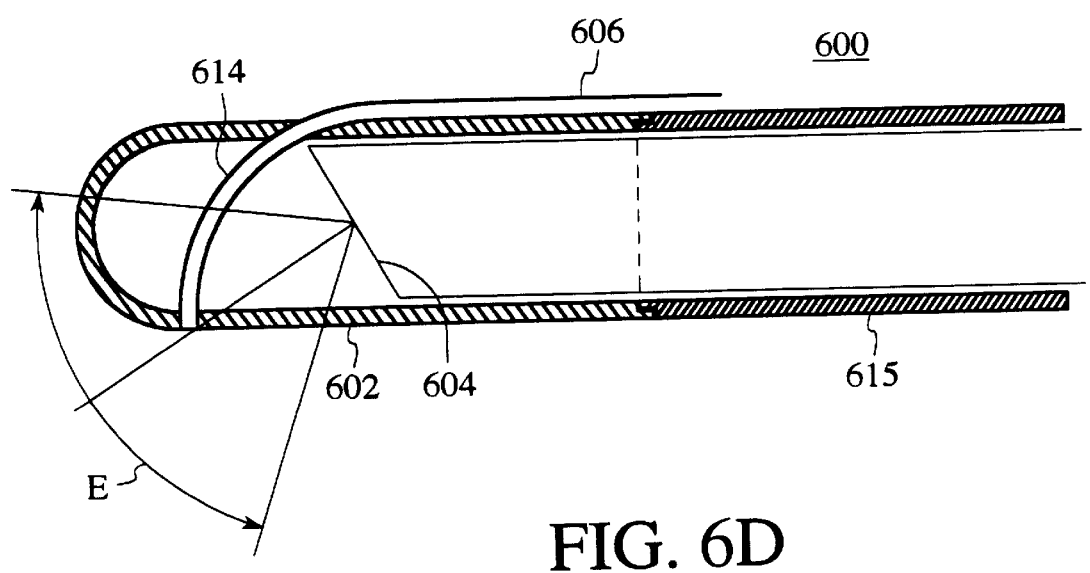

FIGS. 6A–D are representative section views of variations of a viewing tubular assembly 600. The assembly 600 can be used with either a flexible or rigid endoscope. In particular, the assembly 600 as used with the viewing surgical scope 100 replaces the flexible distal end assembly 115 as shown in FIG. 1A; or alternatively and preferably used with a rigid shafted endoscope 200 discussed below and representatively shown in FIGS. 8A & 8B. The viewing tubular assembly 600 includes an optically clear or transparent end tube cap 602 which fits over the visualization port distal end 604 of a scope's visualization shaft and has a working channel 606 (cut-off view). The distal ends 604 in FIGS. 6A & 6B lie in planes essentially perpendicular to the central axis of the viewing tubular assembly 600 such that optics provide essentially direct forward visualization with a predetermined divergence viewing angle E as shown. The end port 604 shown in FIG. 6C is at a 30° angle with respect to the central axis of the viewing tubular assembly 600. Distal end 604 can be varied such that the field of view is at an angle offset with respect to the central axis of viewing tubular assembly 600. The viewing tubular assembly 600 replaces the components of flexible member 114 and cup member 116 in FIGS. 2A–2C and cooperatively combines with the shaft member 112 and connectively interfaces representatively with the working channel 134 with appropriate tubing connectors with the working channel 606 shown in FIGS. 6A–6D. The end cap 602 member is made from an acrylic or equivalent polycarbonate transparent material and coupled to a rigid tubular sleeve member 615. Moreover, the assembly 600 can be a solid object made of the same material as the end cap 602 member. The distal end of the visualization scope 604 terminates near the transparent end cap 602. The end cap 602 can made with desired optical light absorption/reflection characteristics. Furthermore, the shape of the end cap 602 can be conical, elliptical or include planar facets at various angles with respect to the viewing tubular assembly's 600 central axis. The end cap 602 is designed and made in accordance with required optical lens characteristics such as focus, divergence, convergence, directionability, collimation, polarization or diffusion.

Figure 8A:
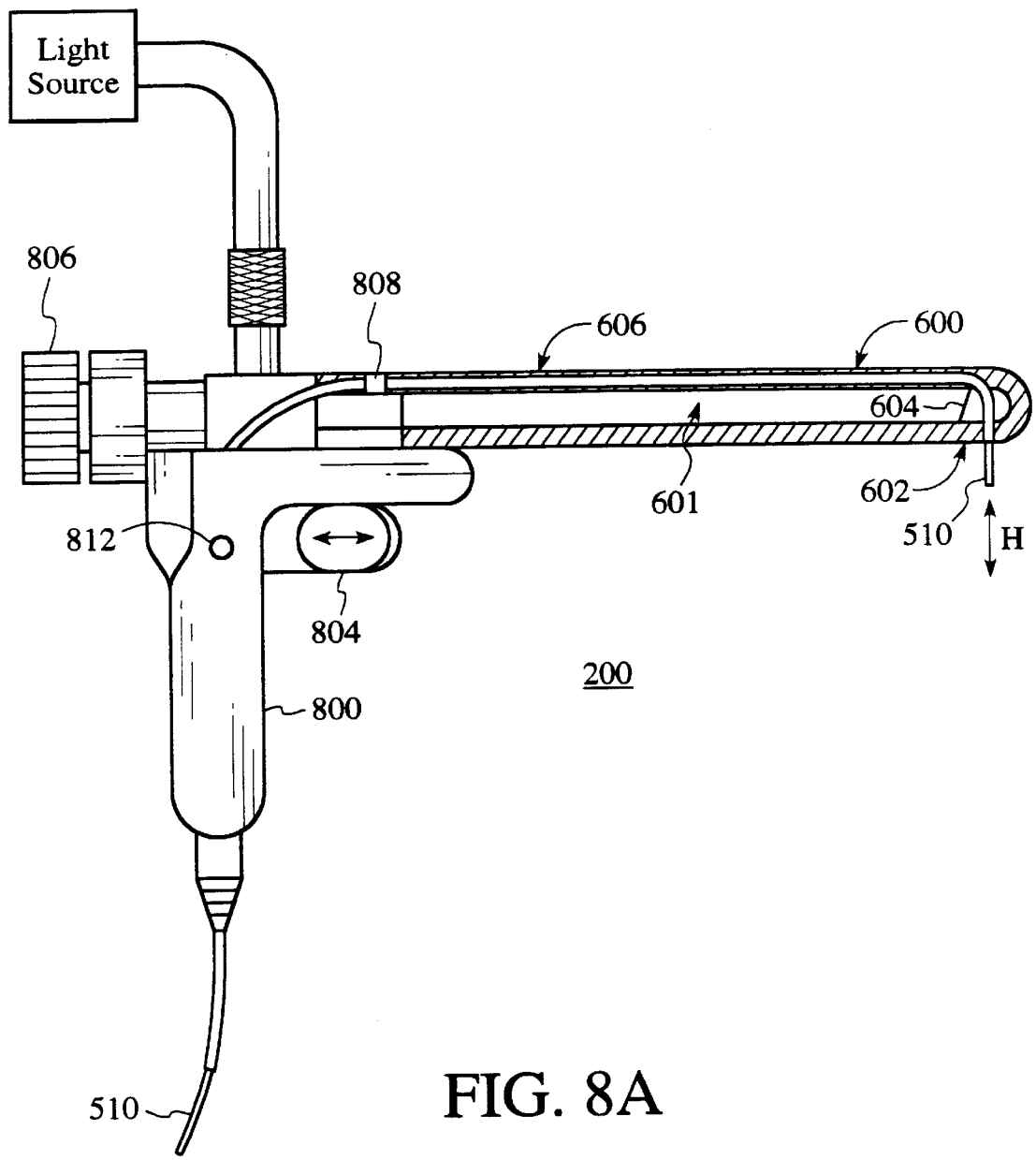
FIGS. 8A is a second viewing surgical scope apparatus embodiment of the invention using a non-articulating viewing surgical scope that includes the clear distal tip tubular member shown in FIGS. 6A–6D.

The working channel 606 has various designs with differing bends that cooperatively are attached to the viewing tubular assembly 600. The working channel 606 as shown is external to the assembly 600, but can be incorporated into a lumen or be a structural tube either in the wall of the viewing tubular assembly 600 or conformably designed to fit within the inner wall surface of assembly 600 adjacent the distal end 604 of the visualization scope 342 or an end shaft of a rigid or flexible endoscope. The working channel 606 is shown attached to the external wall of assembly 600 in FIGS. 6A–6D. Viewing tubular assembly 600 functions to allow viewing of affected tissue while applying pressure to tissue for stopping bleeding and minimizing active tissue movement, e.g. a beating heart. The working channel 606 directs and protects the operative working device such as the optical fiber element 510, a drug delivery needle or other energy delivery device that is controlled by handle 800 as shown in FIGS. 8A. The working channel 606 can be made of stainless steel, plastic or comparable material. In the preferred embodiment, the working channel 606 is clear to enable visualization of fiber movement. The working channel 606 in FIG. 6A has a curvature 608 such that the fiber or other working device is directed through the transparent end cap 602 in a direction essentially parallel with/or contiguous with respect to the central axis of the assembly 600. The working channel 606 has a curvature 612 in FIG. 6B which directs the working device through the transparent end cap 602 at approximately 45° with respect to the central axis of the assembly 600. Likewise, the curvature 614 in the working channel 606 of FIG. 6C directs the working device through the transparent end cap 602 in a direction approximately 90° with respect to the central axis of the viewing tubular assembly 600. Other orientations of working channel 606 and/or distal end bends in tube 606 can be used to direct the working device.

Figure 7:
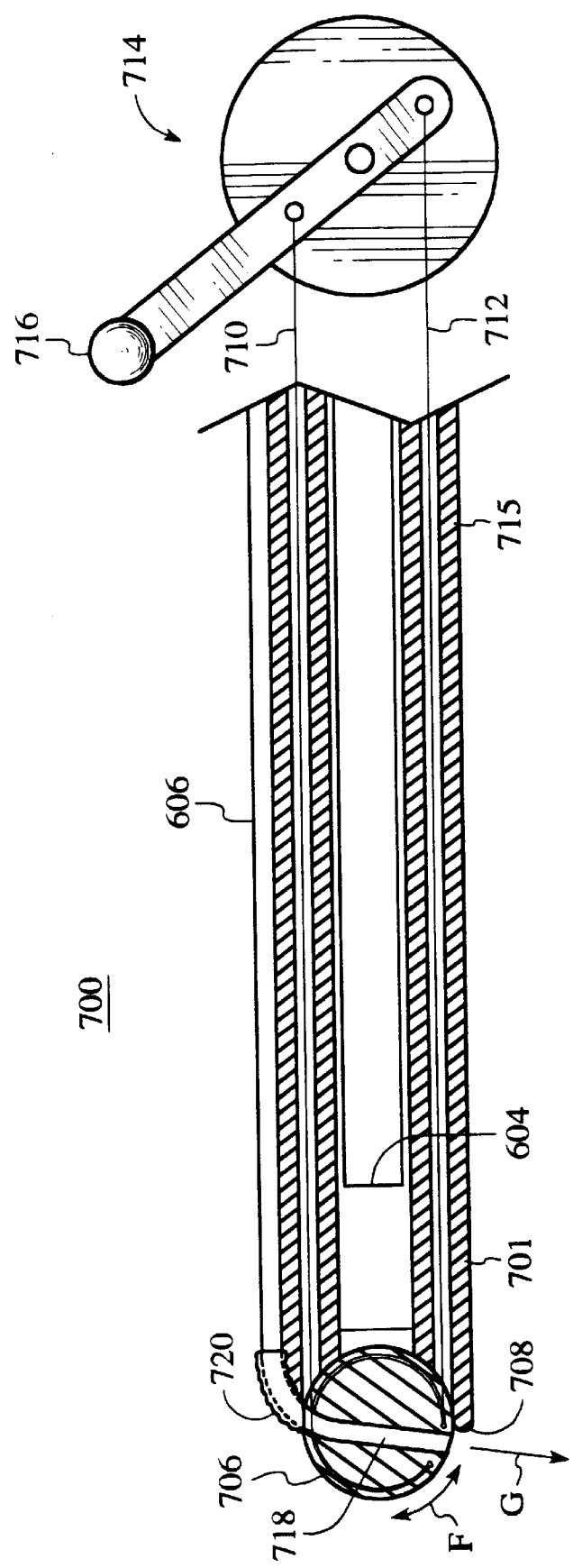
FIG. 7 is a representative section view of a variation to the clear distal tip tubular member as shown in FIGS. 6A–6D that has elements's for controlling the working device's orientation at the viewing surgical scope's distal end.

FIG. 7 is a representative section view of a variation of a movable distal ended optical ball viewing tubular assembly 700 that provides variable positioning of the working device such as the optical fiber 510 and can also be part of either viewing surgical scope 100 or 200 as discussed below. The optically transparent rotatable member 706, which is either a ball or cylinder member, is at the distal end 708 and seats within a conformal shaped end tube 701 that allows free rotation of the rotatable member 706. Upper steering wire 710 and a lower steering wire 712 are coupled to the rotatable member 706. The steering wires 710 and 712 pass back to a proximal portion of the scope 100 or 200 to control mechanism 714. The steering wires 710 and 712 are coupled to deflector knobs 716 for rotating the rotatable member 706 in a direction as shown by double headed arrow F. A guide channel 718 passes through the rotatable member 706. A flexible coupling portion 720 extends between the guide channel 718 of the rotatable member 706 and the working channel 606, thereby providing a path for directing the working device such as an optical fiber 510 therethrough. Flexible coupling portion 720 is a telescoping or an accordion-like interconnection allowing reorientation of the rotatable member 706 to direct the working device in a direction G. Tensioning steering wire 710 rotates the rotatable member 706 and re-directs the guide channel 718 in opposition to steering wire 712. Additionally, more control wires can be includes to provide multiple degrees of rotation of the rotatable member 706 for greater controllability.

The articulating distal ended viewing tubular assembly 700 can replace the components of flexible member 114 and cup member 116, i.e. assembly 115 in FIGS. 2A–2C and cooperatively slides on shaft member 112. The viewing tubular assembly 700 connectively interfaces at least with the conduits 130 and 134 with appropriate tubing channeling connectors and by appropriate internal control wire connections within the proximal end of sleeve member 715 and to appropriate connections in the flexible catheter shaft 120. Moreover, the catheter 120 can be a stand alone viewing device whose distal end which representatively can be 604 in FIG. 7 and the work channel 606 would be tubing attached to the catheter 120 shafting. The viewing surgical scope 200 discussed below and shown as FIG. 8A and 8B would have a control member 714 on the handle 800 with connecting control wires 710 & 712. The assembly 700 would encompass the rigid endoscope shafting 601 as discussed below.

The articulating assembly 700 of FIG. 7 can have alternative designs such as an assembly comprising an internal mechanical deflecting linkage mechanism for changing the orientation of the egression angle of the working channel 606. The transparent surface rotatable member 706 would be replaced with an essentially transparent cap member comparable to 602 with a flexible membrane to allow orientation displacement of the working channel 606 that is sealed within the membrane. Moreover, the deflecting linkage mechanism can be a light reflecting surface such that observations of tissue can be at offset angles with respect to the axial direction of the assembly tube 715 where the distal end of the visualization scope 604 has a normal surface with respect thereto.

FIG. 8A shows viewing surgical scope 200 with a handle assembly 800 using a finger trigger advance mechanism 804 and has the tubular viewing assembly 600. The assembly 600 is non-articulating distal clear end cap 602 for visualizing and has a working channel 606 for directing the working device, e.g. an optical fiber 510 at a treatment site. The visualization scope is an endoscope whose distal end 604 is viewed through an eyepiece 806. The distal end 604 of the endoscope can have different angular orientations as discussed above for a required distal end viewing field from the viewing tubular assembly 600. The viewing surgical scope 200 for example can be a 10-mm sized rigid endoscope with a viewing tubular assembly 600 that has a 12 mm-O.D. A smaller 5-mm system endoscope, can also be used where the assembly 600 is about 10–12 mm O.D. that allows for additional space inside the assembly 600 for additional working channels 606 that allow for drug delivery, lighting etc. The handle assembly 800 is ergonomically designed for hand gripping. The handle assembly 800 includes a fiber advance mechanism using finger trigger 804 within the handle and alignment retaining members for attaching endoscope shafting 601 along with the viewing tubular assembly 600. The viewing tubular assembly 600 is user removable for quick disconnect from the endoscope shafting 601 for quick interchange of tubular assemblies 600 with different working channel 606 egress angles for surgical procedures that occur at various aspects of the heart surface, such as the lateral, anterior, posterior or apexial walls when operating from a single chest penetration. The viewing tubular assembly 600 has a quick disconnect coupling member 808 for connections of the working channel 606 for quick interchangeability of the assembly 600. Additionally, the articulated viewing tubular assembly 700 shown in FIG. 7 can be used with the necessary control features incorporated within the handle 800. This feature allows access to lateral, anterior or posterior locations of an organ where a practitioner uses the same chest wall penetration.

Finger trigger 804 controls translatable movement of the working device, e.g. an optical fiber element 510 with or without a piercing needle distal end assembly 500 as shown in FIG. 5. The finger trigger 804 actuates mechanical or electrically movement of the working device from the distal end of the viewing tubular assembly 600 shown by the double arrow H, preferably using incremental control. Mechanisms for the advancement/retraction function include rack and pinion components, a stepper motor with appropriate control, pneumatic driven mechanisms with incremental stepping functional components.

Figure 8B:
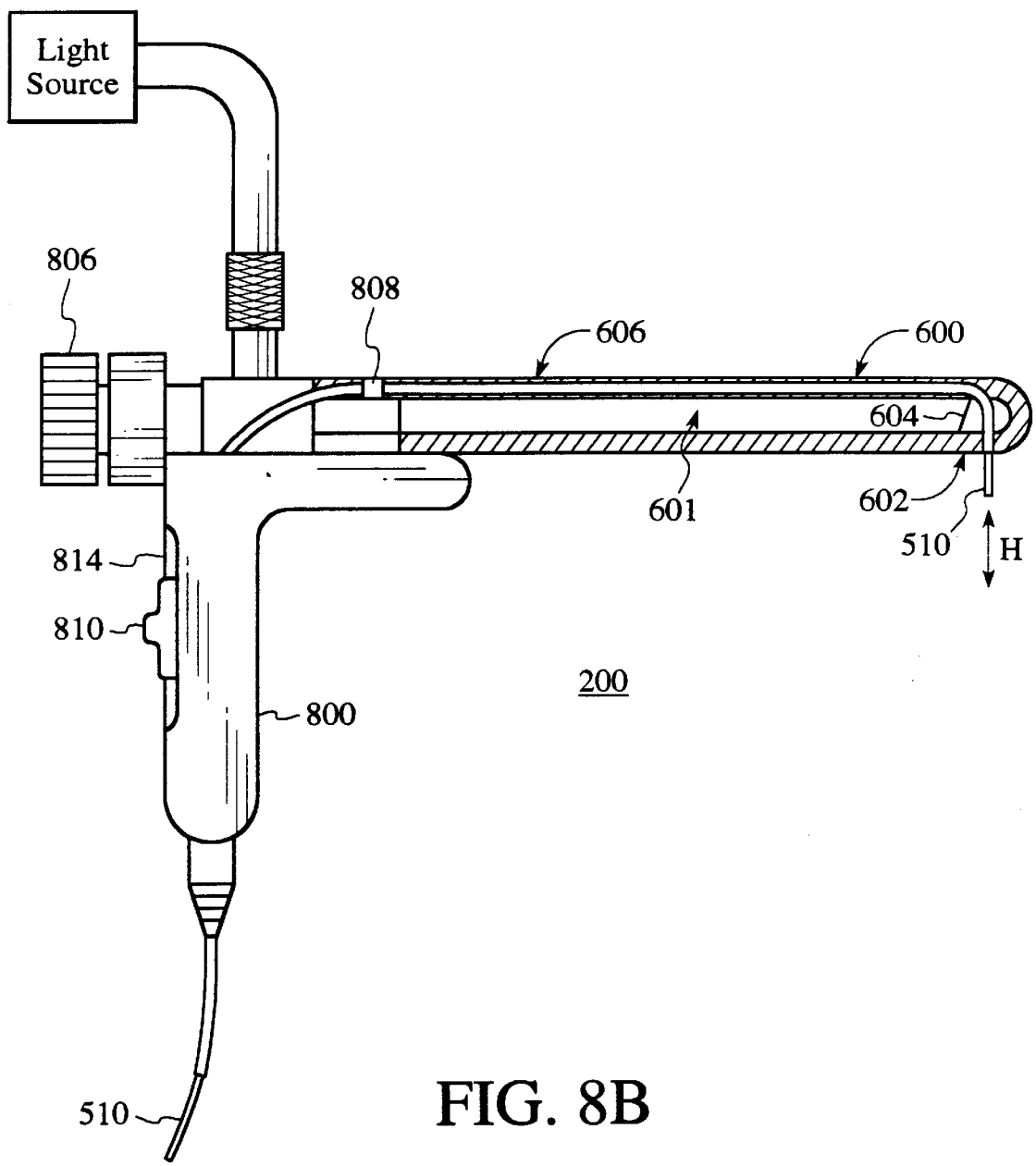
FIGS. 8B is a variation of the second viewing surgical scope embodiment of the invention using a non-articulating viewing surgical scope that includes the clear distal tip tubular member shown in FIGS. 6A–6D where the handle uses a sliding advance mechanism for the working device.

Alternatively, the handle can include a slide member 810 as shown in FIG. 8B which can include a mechanism comparable to that discussed above in FIGS. 4A & 4B wherein a triggering mechanism advances a needle piercing member 500 and cooperatively works with the optical fiber 510 through an adjustable range, e.g.1.5–2.5 cm. The slide member 810 can include detents for a user to sense rate of advancement. The advancement mechanism can also be geared to provide advancement at translation ratios other than 1:1. Retraction of the optical fiber 510 can be accomplished by reversing the trigger button 812 that cooperates with a reversing rack mechanism inside handle 800. A stop setting member 814 can be used to position the optical fiber distal ending flush with the viewing tubular assembly's 600 outer surface. Alternatively, the mechanisms shown in FIGS. 4A & 4B showing a slide controlled mechanism could be incorporated in handle 800 in lieu of the finger trigger 804. An equivalent lever mechanism can be used in lieu of the finger trigger 804 which would include stops to limit optical fiber extension and retraction. In a TMR operation, the optical fiber element 510 would typically would be advanced in 1-mm increments.

Figure 9:
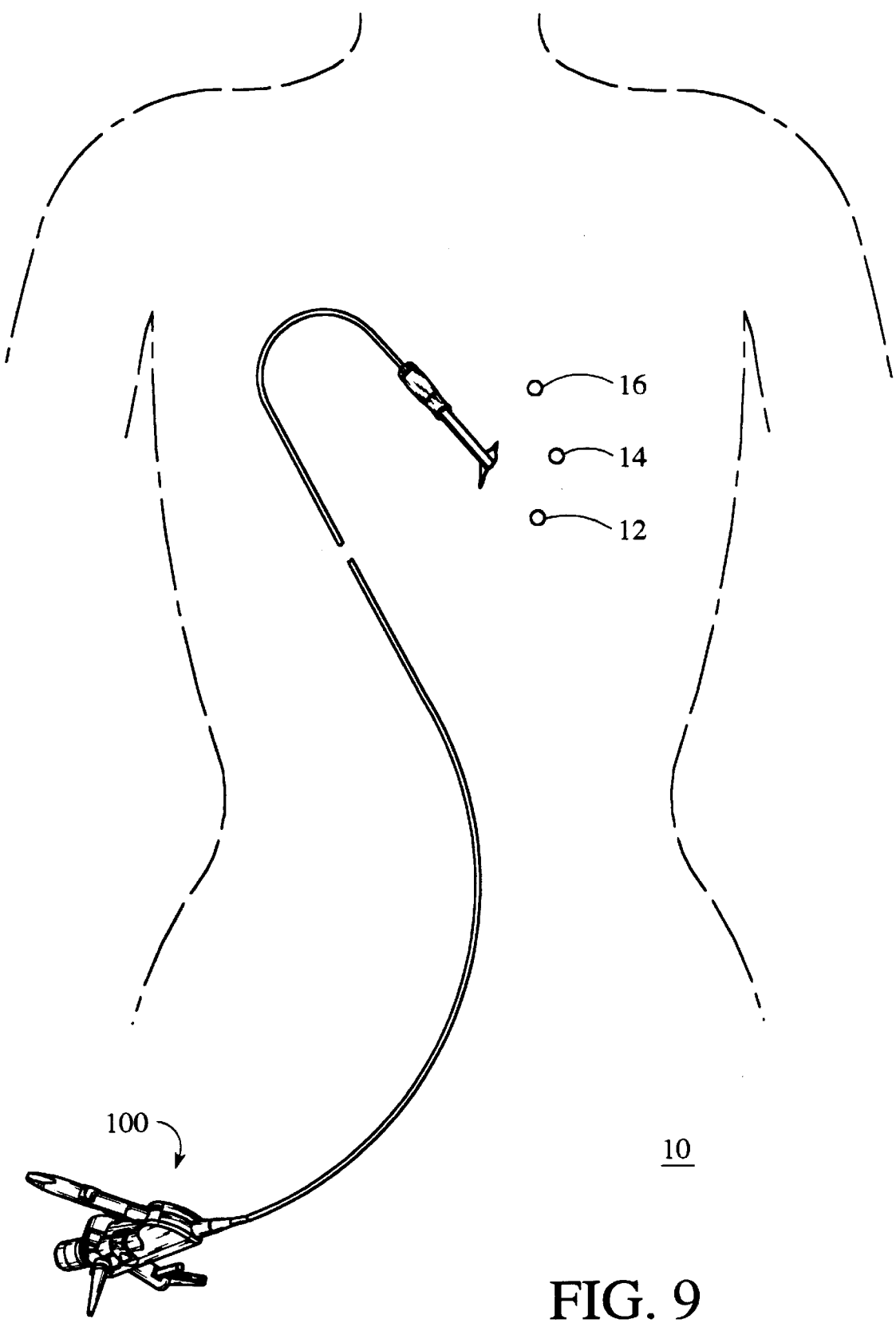
FIG. 9 is a perspective view of a patient illustrating first, second and third minimally invasively formed penetrations formed in the patient's chest, such as used for access in TMR.

FIG. 9 shows a perspective view of a patient 10 with first, second and third minimally invasive formed penetrations 12, 14 and 16 respectively. It will be appreciated that the exact location of penetrations 12, 14 and 16 is not limited to those illustrated in FIG. 9. Additionally, from 1 to N+1 numbers of penetrations may be made. The patient is prepared for the procedure and is positioned similarly to that used for a left thoracotomy. The patient's left arm is draped. A conventional double lumen endotracheal tube is used to selectively deflate one side or the other of the lungs. Preferably the left lung is collapsed which allows access to the chest cavity in the vicinity of the left lung. The other lung remains inflated to provide oxygenation.

The distal portion of either viewing surgical scope 100 or 200 is positioned to reach a desired aspect of a ventricular wall. A plurality of different revascularization channels are formed in the heart. A distal portion of the energy delivery device or other working device can be positioned against tissue of the wall of the heart through which the channel is to be formed while transmitting energy from a remote energy source through the optical fiber element 510 or other energy delivery device. Additionally, the waveguide may be configured to pierce the epicardium, such as with a piercing needle as shown in FIG. 5, so that energy is or can be subsequently delivered to the myocardium. A revascularization channel can be formed through an epicardium into at least a portion of a myocardium or continue through the myocardium into all or only a portion of the endocardium.

In one method, penetration 12 is used for the introduction of either scope 100, 200 or a separate rigid scope to provide global viewing capability of an internal chest area of interest. For standard TMR at the apex 20 region of the heart, a first penetration 12 can be formed in the intercostal spaces, for example the fourth to sixth intercostal space that is 10–12 mm in diameter. A slight cut is made and a thoracic trocar is advanced through the chest.

The scope 100, 200 or separate rigid visualization scope is used to visualize the area, look for larger coronary vessels, to inspect the condition of the pericardium, and to check for adhesions. The shape of the heart as well as its position is visualized. Second penetration 14 is formed inferior to penetration 12 and can be formed just above the diaphragm and third penetration 16 is formed superior to penetration 12. Penetrations 14 and 16 can be formed substantially the same way as penetration 12 is formed or may be cut downs only.

Figure 10:
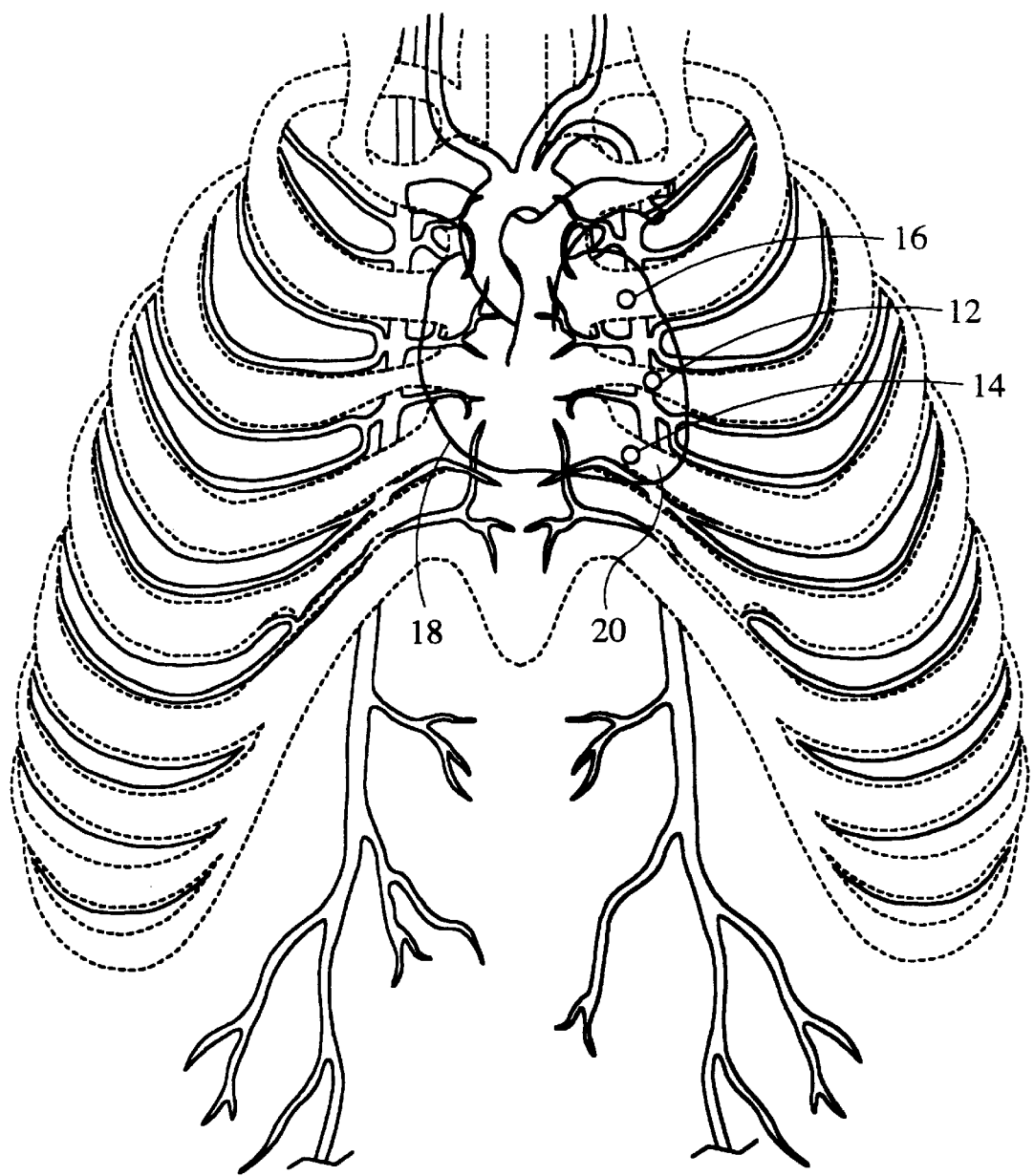
FIG. 10 is a perspective view of an interior of the patient's chest shown in FIG. 9.

For initial procedures a pair of thoracoscopic graspers may be introduced through penetration 14. Additional tools that can be introduced through penetration 14 include scissors. The pericardial sac 18 shown in FIG. 10, if intact, is grabbed and opened up using standard surgical techniques. The pericardial sac is pulled away from the heart and may be suspended. Unwanted adhesions are removed.

After the tools are removed from penetration 14, either scope 100 or 200 with a working channel is introduced where the visualization scope, either a bronchoscope 342 or an endoscope can use a camera device attached to the eyepiece for viewing on a monitor. Additionally, additional viewing scope devices can be used during the procedure as inserted in the first penetration and the rigid scope can be inserted into second penetration 14 after the tools are removed from second penetration 14.

Third penetration 16 is formed, a trocar introduced and a pair of forceps places an absorbing medium, including but not limited to a piece of gauze, through the third penetration 16. Third penetration 16 is created initially to open the pericardial sac and subsequently may be used as a treatment port, for visualization or for safety reasons. In the event that a structure, such as a coronary artery is nicked and bleeding is initiated, direct pressure is applied by placing the gauze on the area through third penetration 16 to stop the bleeding. The gauze is also useful for manipulating the heart and applying slight pressure to TMR entrance sites to avoid excessive bleeding. When using the scope 200, the tubular member assembly 600 stops bleeding when applied to areas undergoing treatment.

Either of the viewing surgical scopes 100 or 200 shown in FIGS. 1A, 8A or 8B is initially positioned in penetration 14 and revascularization channels are created at the desired location, such as the apex 20. Preferably the working device such as the energy delivery device is inserted through the working channel of either of the scopes 100 or 200 adapted for the procedure. The articulating-type scope 100 also may be initially positioned in penetration 12 or 16. Once the desired number of revascularization channels are formed, either of the scopes 100 or 200 can be removed and positioned in any of the other penetrations. Graspers and needle holders, or other instruments, are introduced through one of the penetrations to stitch back the pericardial sac as required. A check is made to ensure that there is no bleeding, trocars are removed and the penetrations closed. It will be recognized that the procedure will vary, depending upon the condition of the heart and the site of the procedure.

In the preferred use of the present invention, the distal portion of the working device such as the energy delivery device is positioned to reach a desired aspect of a ventricular wall. A plurality of different revascularization channels are formed in the heart. A distal portion of the energy delivery device can be positioned against tissue of the wall of the heart through which the channel is to be formed while transmitting energy from a remote energy source through the energy delivery device.

Suitable working devices that can be inserted in the working channels of viewing surgical scopes 100 or 200 include energy delivery devices which include laser wave guides, RF electrodes, microwave cutters, ultrasound transmitters, mechanical coring devices or fluid jets. Each energy delivery device is configured to be coupled to an energy source including but not limited to RF, laser, microwave, ultrasound, mechanical coring, fluid jet, cryogenic fluid, chemical ablation and the like. The distal portion of the working device such as an energy delivery device can be positioned next to the heart wall while energy is delivered through the energy delivery device. Alternatively, the energy delivery device can deliver energy through a gaseous medium to the heart wall. The scopes 100 or 200 distal end can include a piercing obturator member for initial entry between the pericardial sac and the epicardium so that energy is delivered into the myocardium with minimal tissue destruction. A revascularization channel can be formed through an epicardium into at least a portion of a myocardium or continue through the myocardium into all or only a portion of the endocardium.

Other surgical procedures that scopes 100 or 200 could be used include gall bladder, laparoscopy or laparotomy, colosectomy and other MIS operations that use other working devices for treatment of diseased tissue, such devices structurally configured for a working channel.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

What is claimed is:

1. A minimally invasive surgical apparatus comprising:
   a rigid tubular introducer having a proximal portion, an essentially transparent distal portion comprising an end cap, and a lumen housing a distal portion of a visualization device; and
   at least one working tube defining a working channel in combination with the introducer having proximal and distal portions and a terminus at the distal portion of the introducer, the working channel configured to house an egressible working device for effectuating a minimally invasive surgical procedure, whereby the distal portion of the at least one working tube and a target tissue site are viewable at a proximal end of the visualization device when the distal portion of the introducer engages the target tissue.

2. The apparatus of claim 1 wherein the distal portion of the introducer has a conical shape.

3. The apparatus of claim 1 wherein the introducer is essentially transparent.

4. The apparatus of claim 1 wherein at least the distal portion of the working channel is essentially transparent to enable visualization of the working device.

5. The apparatus of claim 4 wherein the working channel is essentially transparent.

6. The apparatus of claim 1 wherein the proximal portion of the working channel is attached to an external surface of the introducer and the distal portion of the working channel is within the rigid introducer.

7. The apparatus of claim 6 wherein the distal portion of the working channel is at an angle to the proximal portion of the working channel.

8. The apparatus of claim 1 wherein the proximal and distal portions of the working channel are within the rigid introducer.

9. The apparatus of claim 1 wherein the proximal portion of the working channel is within a wall of the rigid introducer.

10. The apparatus of claim 1 wherein the working channel is within the lumen of the rigid introducer.

11. The apparatus of claim 1 further comprising a second working channel configured to house an egressible working device.

12. The apparatus of claim 1 further comprising a shaft having proximal and distal portions and at least one working channel coupled to the proximal portion of the rigid introducer, a first of the at least one working channel of the rigid introducer being coupled to a first of the at least one working channel of the shaft.

13. The apparatus of the claim 12 further comprising a handpiece having a working device advancement mechanism and an actuation member, said handpiece coupled to the proximal portion of the shaft.

14. The apparatus of claim 12 wherein the shaft further comprises a second working channel and the rigid introducer further comprises a second working channel.

15. The apparatus of claim 12 wherein the shaft further comprises two or more working channels and the rigid introducer further comprises two or more working channels, each working channel of the shaft coupling to a corresponding working channel of the introducer.

16. The apparatus of claim 12 further comprising a body member operably attached to the proximal portion of the shaft.

17. The apparatus of claim 16 wherein the body member comprises an actuation device for controlling the operation of the working device.

18. The apparatus of claim 17 wherein the actuation device comprises a movement mechanism for moving the working device, whereby the distal portion of the working device moves with respect to the point of egression from the rigid introducer in response to movement of the movement mechanism.

19. The apparatus of claim 18 wherein the shaft is essentially flexible.

20. The apparatus of claim 18 wherein the shaft is essentially rigid.

21. The apparatus of claim 18 wherein the end cap is rotatable, the end cap comprises an internal channel which communicates with the at least one working tube, the body member further comprises a means for controlling the orientation of the rotatable end cap thereby variably controlling the point of egression of the working channel.

22. The apparatus of claim 17 wherein the first of at least one working tube comprises a concentric working tube having a proximal and a distal portion having a piercing needle assembly, the first of at least one working tube being independently slidably disposed within the concentric working tube, the movement mechanism comprising a triggering device for actuating the piercing needle assembly.

23. The apparatus of claim 22 wherein the working device is at least one fiber optic element.

24. The apparatus of claim 1 wherein the working device is a laser energy delivery device.

25. The apparatus of claim 24 wherein the laser energy delivery device is at least one fiber optic.

26. The apparatus of claim 25 further comprising a piercing needle assembly in combination with the laser energy delivery device.

27. The apparatus of claim 26 wherein the piercing needle assembly comprises a flexible portion.

28. The apparatus of claim 27 wherein the piercing needle assembly is a drug delivery device.

29. The apparatus of claim 1 wherein the working device is a piercing needle assembly.

30. The apparatus of claim 29 wherein the piercing needle assembly comprises a flexible portion.

31. The apparatus of claim 30 wherein the piercing needle assembly is a drug delivery device.

32. The apparatus of claim 1 wherein the working device is a coring device.

33. The apparatus of claim 1 wherein the working device is a drug delivery device.

34. The apparatus of claim 33 further comprising a piercing needle assembly in combination with the drug delivery device.

35. The apparatus of claim 1 wherein the visualization device is rigid.

36. The apparatus of claim 1 wherein the visualization device is essentially rigid.

37. The apparatus of claim 1 wherein the visualization device is flexible.

38. The apparatus of claim 1 wherein the longitudinal axis of the distal portion of the at least first working channel and the longitudinal axis of the introducer are the same.

39. The apparatus of claim 1 wherein the longitudinal axis of the distal portion of the at least first working channel and the longitudinal axis of the introducer define an angle therebetween.

40. The apparatus of claim 39 wherein the angle is 0°.

41. The apparatus of claim 39 wherein the angle is greater than 0°.

42. The apparatus of claim 1 wherein the proximal portion of the rigid introducer comprises a handle member having a locking means for mechanically securing the at least one working tube to the rigid introducer.

43. The apparatus of claim 1 wherein a distal end of the visualization device defines a planar surface, whereby a line normal to the planar surface and the longitudinal axis of the rigid introducer defines a first angle.

44. The apparatus of claim 43 wherein the longitudinal axis of the working channel at the point of egression and the longitudinal axis of the introducer defines a second angle.

45. The apparatus of claim 44 wherein the first angle is about 0° and the second angle is equal to or greater than 0°.

46. The apparatus of claim 44 wherein the first angle is greater than about 0° and the second angle is equal to or greater than 0°.

47. The apparatus of claim 44 wherein the first angle is equal to or greater than 0° and the second angle about 0°.

48. The apparatus of claim 44 wherein the first angle is equal to or greater than 0° and the second angle is greater than 0°.

49. The apparatus of claim 44 wherein the rigid introducer further comprises a connection means for mating the distal portion of the rigid introducer to the proximal portion of the rigid introducer, a first distal portion of the rigid introducer being able to be quickly disconnected and replaced with a second distal portion, the second angle of the second distal portion being different from the second angle of the first distal portion.

50. A surgical procedural apparatus for visualizing and treating tissue in a minimally invasive surgical procedure, the apparatus comprising:
   a visualization scope having a proximal portion comprising a body member, and an elongated sleeve member configurably attached to the body member and having a distal portion housing a visualization device; and
   a rigid introducer and viewing assembly comprising:
      a tubular member, the distal portion of the elongated sleeve member being sidably disposed within the tubular member;
      at least one working tube defining a working channel configured to house a working device; and
      an inelastic and essentially transparent distal portion comprising an end cap which encloses a distal portion of the tubular member, a distal end of the working tube being operably attached to the end cap, whereby the distal portion of the at least one working tube and a target tissue site are viewable at a proximal end of the visualization device when the distal portion of the introducer engages the target tissue.

51. The apparatus of claim 50 wherein the visualization scope and sleeve member are rigid and the distal portion of the working channel has a terminus at the tip member.

52. The apparatus of claim 50 wherein the visualization scope is a bronchoscope, the sleeve member is a flexible catheter shaft and the introducer and viewing assembly further includes an essentially rigid outer sleeve member attached to a distal portion of the catheter shaft with a handle member at a proximal portion of the outer sleeve member.

53. The apparatus of claim 50 wherein the tubular member and the tip member are a unitary member having a substantially uniform wall thickness.

54. The apparatus of claim 50 wherein the body member further comprises an actuation device operatively attached to the working device for controlling operation of the working device.

55. The apparatus of claim 54 wherein the actuation device further comprises a movement control, whereby advancement and retraction of the working device out from and into the end cap can be controlled.

56. The apparatus of claim 55 wherein the end cap is rotatable and the end cap comprises an internal channel which communicates with the at least one working tube, the body member further comprises a means for controlling the orientation of the rotatable end cap thereby variably controlling the point of egression of the working channel.

57. The apparatus of claim 55 wherein the at least one working tube further comprises an inner tube member slidably disposed therein defining an internal lumen, a distal end of the inner tube comprising a piercing needle member, the working device independently slidably disposed within the internal lumen of the inner tube member.

58. The apparatus of claim 57 wherein the actuation device further includes a triggering member operatively attached to the inner tube, whereby the piercing member is advanced upon activation of the triggering member.

59. The apparatus of claim 58 wherein the lumen of the piercing needle member contains at least one optical fiber element.

60. The apparatus of claim 59 wherein the working means is an optical fiber element.

61. The apparatus of claim 50 wherein an outer surface of the end cap is convex shaped thereby spreading and stabilizing a surface of target tissue when pressing the assembly against the target tissue and enhancing viewing thereof.

62. The apparatus of claim 50 wherein the longitudinal axis of the working channel at the point of egression and the longitudinal axis of the introducer are the same.

63. The apparatus of claim 50 wherein a distal end of the visualization device defines a planar surface, whereby a line normal to the planar surface and the longitudinal axis of the rigid introducer defines a first angle.

64. The apparatus of claim 63 wherein the longitudinal axis of the working channel at the point of egression and the longitudinal axis of the introducer defines a second angle.

65. The apparatus of claim 64 wherein the first angle is about 0° and the second angle is equal to or greater than 0°.

66. The apparatus of claim 64 wherein the first angle is greater than about 0° and the second angle is equal to or greater than 0°.

67. The apparatus of claim 64 wherein the first angle is equal to or greater than 0° and the second angle about 0°.

68. The apparatus of claim 64 wherein the first angle is equal to or greater than 0° and the second angle is greater than 0°.

69. A method of performing a minimally invasive surgical procedure in a body comprising the steps of:
   a) providing an apparatus comprised of a rigid introducer having a transparent distal portion comprising an end cap and configured to house a distal portion of a visualization device, and at least a first working channel in combination with said introducer, said working channel configured to house an egressible working device for effectuating the procedure, wherein the distal portion of the introducer and a target tissue site are viewable when the distal portion of the introducer engages the target tissue;
   b) introducing the apparatus through a minimally invasive formed penetration;
   c) advancing the working device through the working channel; and
   d) viewing while effectuating the procedure.

70. The method of claim 69 wherein the working device is a laser energy delivery device.

71. The method of claim 70 wherein the procedure is the formation of revascularization channels through at least a portion of the heart wall.

72. The method of claim 71 wherein the procedure is transmyocardial revascularization.

73. The method of claim 71 further comprising an arbitrary step of drug delivery.

74. The method of claim 69 wherein step b) further comprises viewing a treatment site.

75. The method of claim 69 wherein the apparatus further comprises a piercing needle assembly in combination with the working device and prior to step d) further comprising the step of piercing the epicardium.

76. The method of claim 75 wherein the working device is a drug delivery device.

77. The method of claim 69 further comprising the step e) rotating the apparatus and repeating steps c) through d).

* * * * *